United States Patent
Quiachon et al.

(10) Patent No.: US 6,322,587 B1
(45) Date of Patent: *Nov. 27, 2001

(54) BIFURCATED MULTICAPSULE INTRALUMINAL GRAFTING SYSTEM AND METHOD

(75) Inventors: Dinah B. Quiachon, San Jose; Alec A. Piplani, Mountain View; Richard S. Williams; Steve G. Baker, both of Sunnyvale; Peter K. Johansson, San Jose, all of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/097,538

(22) Filed: Jun. 15, 1998

Related U.S. Application Data

(62) Division of application No. 08/698,787, filed on Aug. 16, 1996, now Pat. No. 5,769,885, which is a division of application No. 08/241,476, filed on May 12, 1994, now Pat. No. 5,628,783.

(51) Int. Cl.$^7$ .................................. A61F 2/04; A61F 2/06
(52) U.S. Cl. ....................... 623/1.23; 623/1.36; 623/1.35; 623/903; 606/195
(58) Field of Search ............................ 623/1, 2, 11, 12; 606/194, 195, 198, 191, 192; 604/96

(56) References Cited

U.S. PATENT DOCUMENTS

| | | | |
|---|---|---|---|
| 3,657,744 | 4/1972 | Ersek | 3/1 |
| 4,061,134 | 12/1977 | Samuels et al. | 128/1 |
| 4,108,161 | 8/1978 | Samuels et al. | 128/1 |

(List continued on next page.)

FOREIGN PATENT DOCUMENTS

| | | |
|---|---|---|
| 0 461 791 A1 | 12/1991 | (EP) . |
| 0 508 473 A2 | 10/1992 | (EP) . |
| 0 539 237 A1 | 4/1993 | (EP) . |

(List continued on next page.)

OTHER PUBLICATIONS

Parodi, MD et al. Annuals of Vascular Surgery (1991); pp. 5/6:491–499, "Transfemoral intraluminal Graft Implani Abdominal Aortic Aneurysms".

Chuter, BM, BS et al., Journal of Vascular Surgery (Aug. 1993); pp. 18/2:185–196, "Transfemoral Endovascular Aortic Graft Placement".

*Primary Examiner*—David H. Willse
*Assistant Examiner*—Choon P. Koh
(74) *Attorney, Agent, or Firm*—Fulwider Patton Lee & Utecht, LLP

(57) ABSTRACT

An intraluminal grafting system having a balloon catheter assembly, a capsule catheter assembly and capsule jacket assembly is used for deploying in the vessel of an animal body a bifurcated graft having a plurality of attachment systems. The deployment catheters contain an ipsilateral capsule assembly, a contralateral capsule assembly and a distal capsule assembly, wherein the attachment systems of the bifurcated graft are disposed within the three capsule assemblies. A removable sheath of the capsule jacket assembly covers the bifurcated graft and capsule assemblies to provide a smooth transition along the length of the deployment catheters. The bifurcated graft is comprised of a main tubular member and two tubular legs, having attachment systems with wall engaging members secured to the superior end of the main tubular member and the inferior ends of the tubular legs. An inflatable membrane configured on the balloon catheter is used to firmly implant the attachment systems within the vessel. The bifurcated graft and attachment systems are configured to remain in the vessel after the deployment catheters are withdrawn. The method of use of the present intraluminal grafting system is also disclosed, for example, for deploying a bifurcated graft proximate the abdominal aortic bifurcation.

12 Claims, 14 Drawing Sheets

U.S. PATENT DOCUMENTS

| | | | |
|---|---|---|---|
| 4,140,126 | 2/1979 | Choudhury | 128/325 |
| 4,214,587 | 7/1980 | Sakura, Jr. | 128/334 |
| 4,577,631 | 3/1986 | Kreamer | 128/334 |
| 4,617,932 | 10/1986 | Kornberg | 128/334 |
| 4,728,328 | 3/1988 | Hughes et al. | 623/1 |
| 4,732,152 | 3/1988 | Wallsten et al. | 128/343 |
| 4,739,762 | 4/1988 | Palmaz | 128/343 |
| 4,787,899 | 11/1988 | Lazarus | 623/1 |
| 4,793,348 | 12/1988 | Palmaz | 128/325 |
| 4,795,458 | 1/1989 | Regan | 623/1 |
| 4,830,003 | 5/1989 | Wolff et al. | 128/343 |
| 4,969,896 | 11/1990 | Shors | 623/1 |
| 5,026,377 | 6/1991 | Burton et al. | 606/108 |
| 5,047,050 | 9/1991 | Ardesani | 623/1 |
| 5,078,726 | 1/1992 | Kreamer | 606/194 |
| 5,104,399 | 4/1992 | Lazarus | 623/1 |
| 5,122,154 | 6/1992 | Rhodes | 606/198 |
| 5,123,917 | 6/1992 | Lee | 623/1 |
| 5,192,297 | 3/1993 | Hull | 606/195 |
| 5,201,757 | 4/1993 | Heyn et al. | 606/198 |
| 5,219,355 | 6/1993 | Parodi et al. | 606/191 |
| 5,275,622 | 1/1994 | Lazarus et al. | 623/1 |
| 5,282,824 | 2/1994 | Gianturco | 606/198 |
| 5,316,023 | 5/1994 | Palmaz et al. | 128/898 |
| 5,360,443 | 11/1994 | Barone et al. | 623/1 |
| 5,395,334 | 3/1995 | Keith et al. | 606/194 |
| 5,397,345 | 3/1995 | Lazarus | 623/1 |
| 5,769,885 | 6/1998 | Quiachon et al. | 623/1 |

FOREIGN PATENT DOCUMENTS

| | | |
|---|---|---|
| 0 637 454 A1 | 2/1995 | (EP) . |
| 0 646 365 A1 | 4/1995 | (EP) . |
| 1217402 | 3/1986 | (RU) . |
| 1318235A1 | 6/1987 | (RU) . |
| 1389778A2 | 4/1988 | (RU) . |
| 1457921A1 | 2/1989 | (RU) . |
| 1482714A2 | 5/1989 | (RU) . |
| WO 95/01761 | 1/1995 | (WO) . |
| WO 95/16406 | 6/1995 | (WO) . |

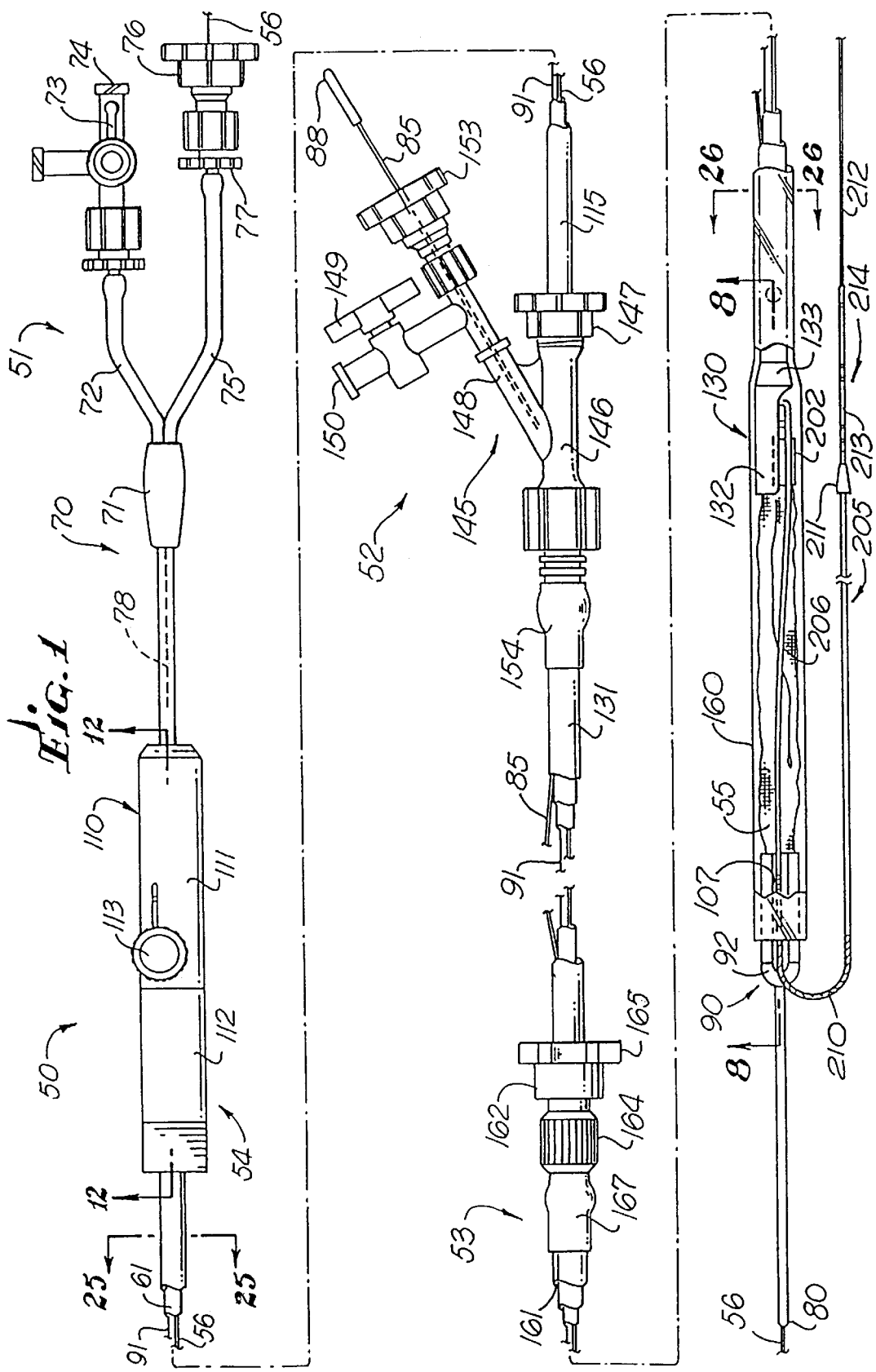

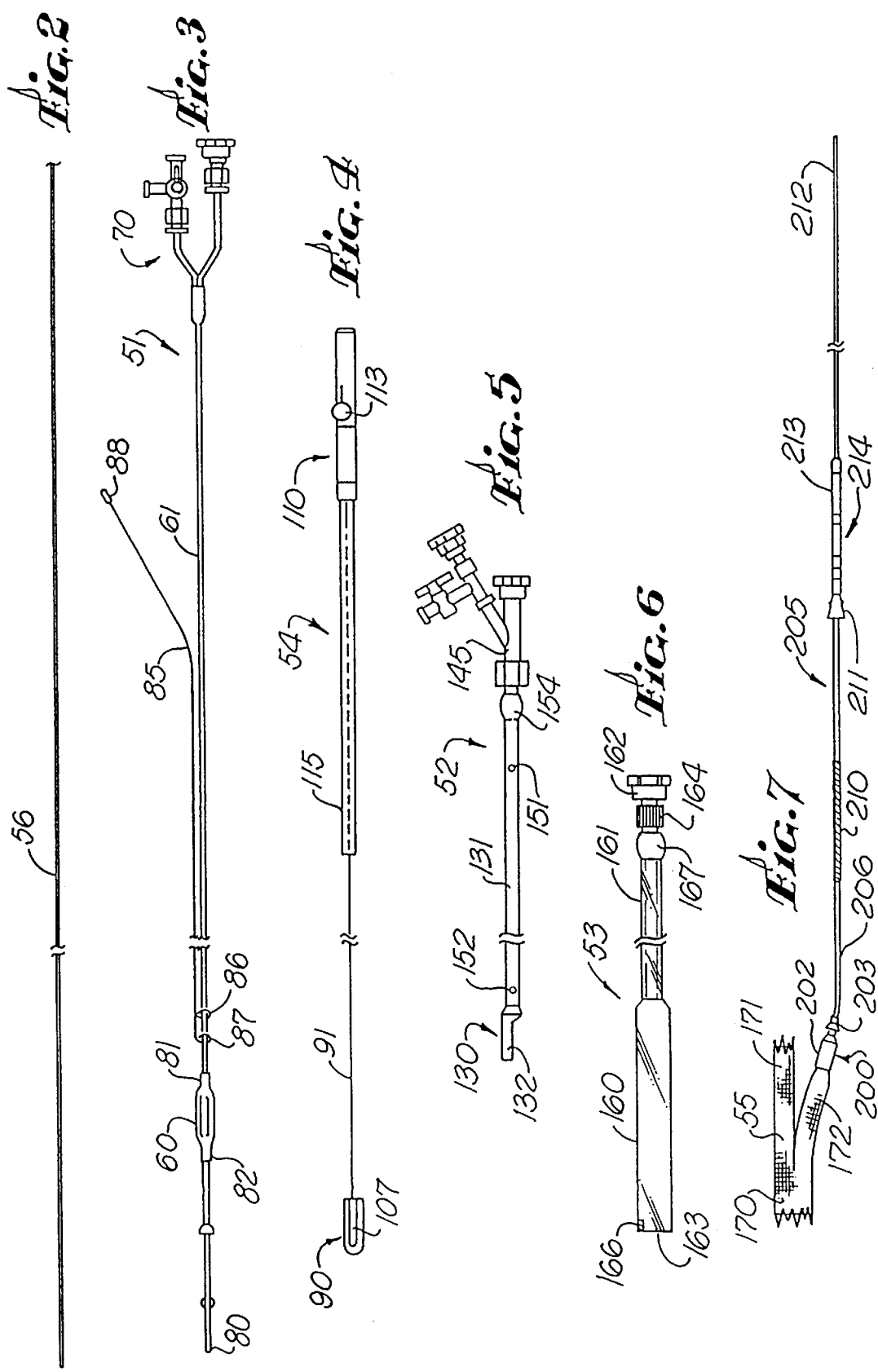

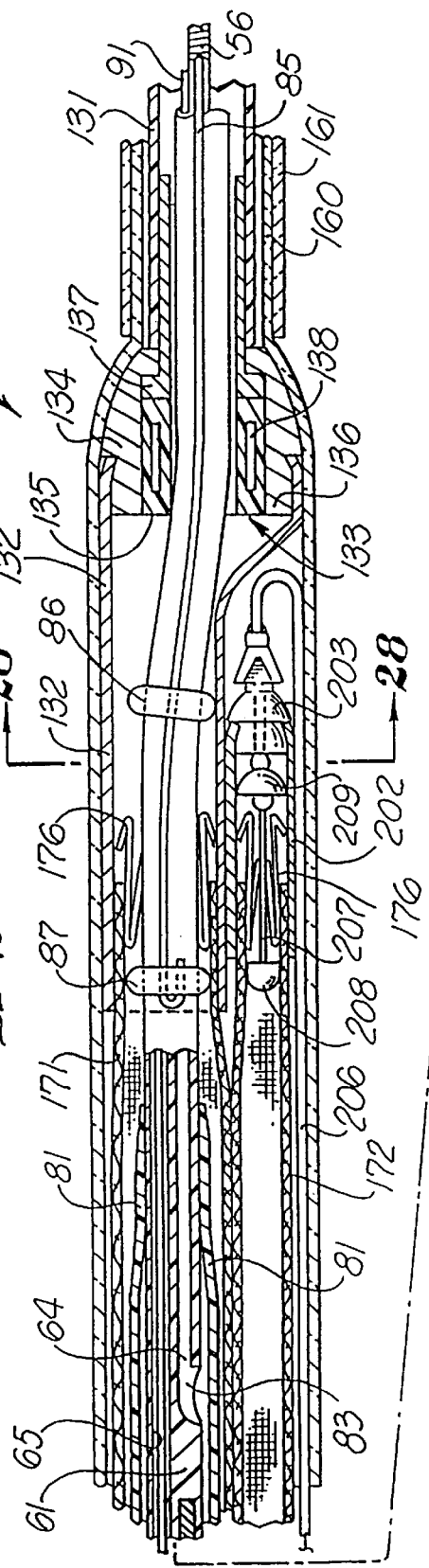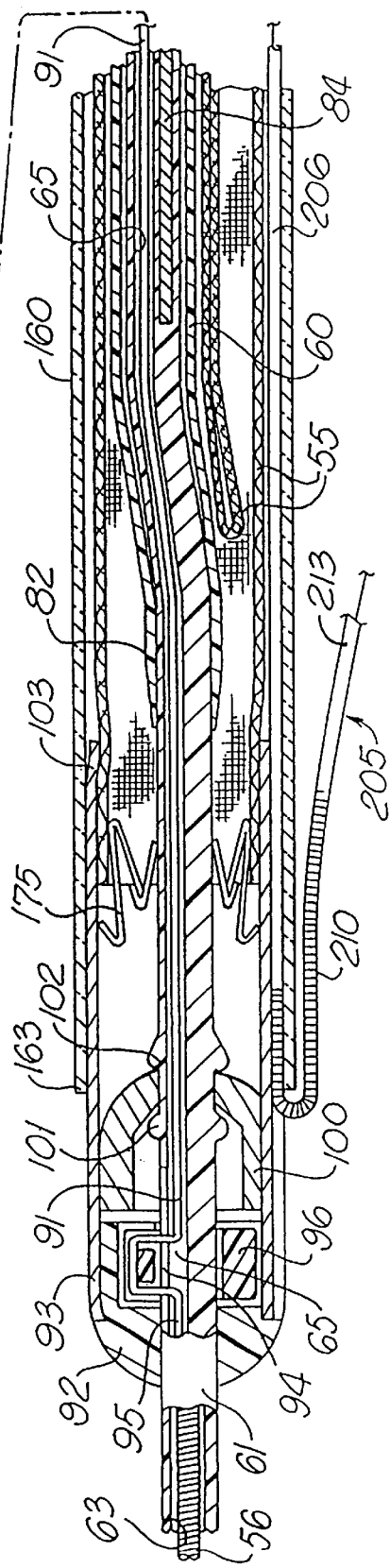
Fig. 8

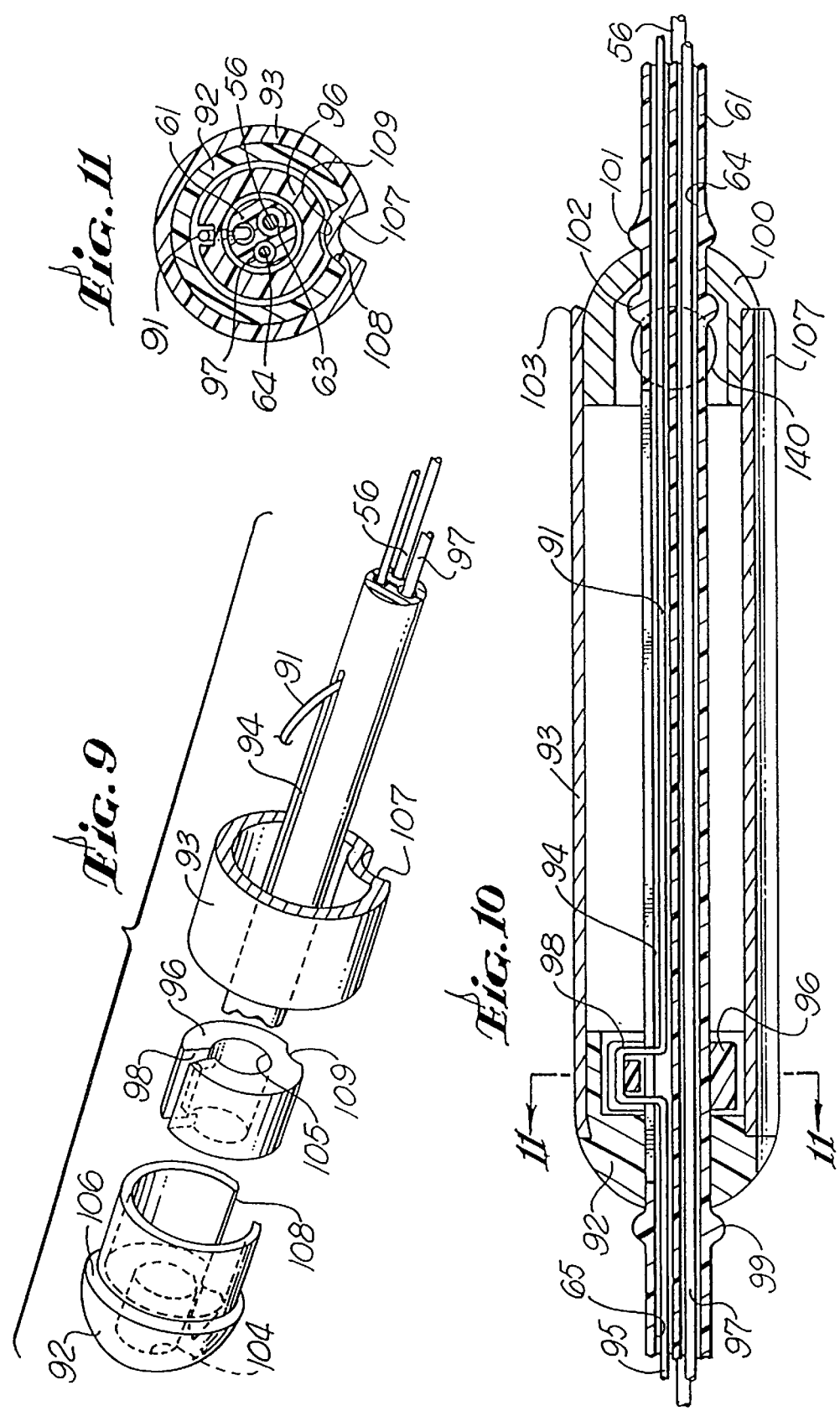

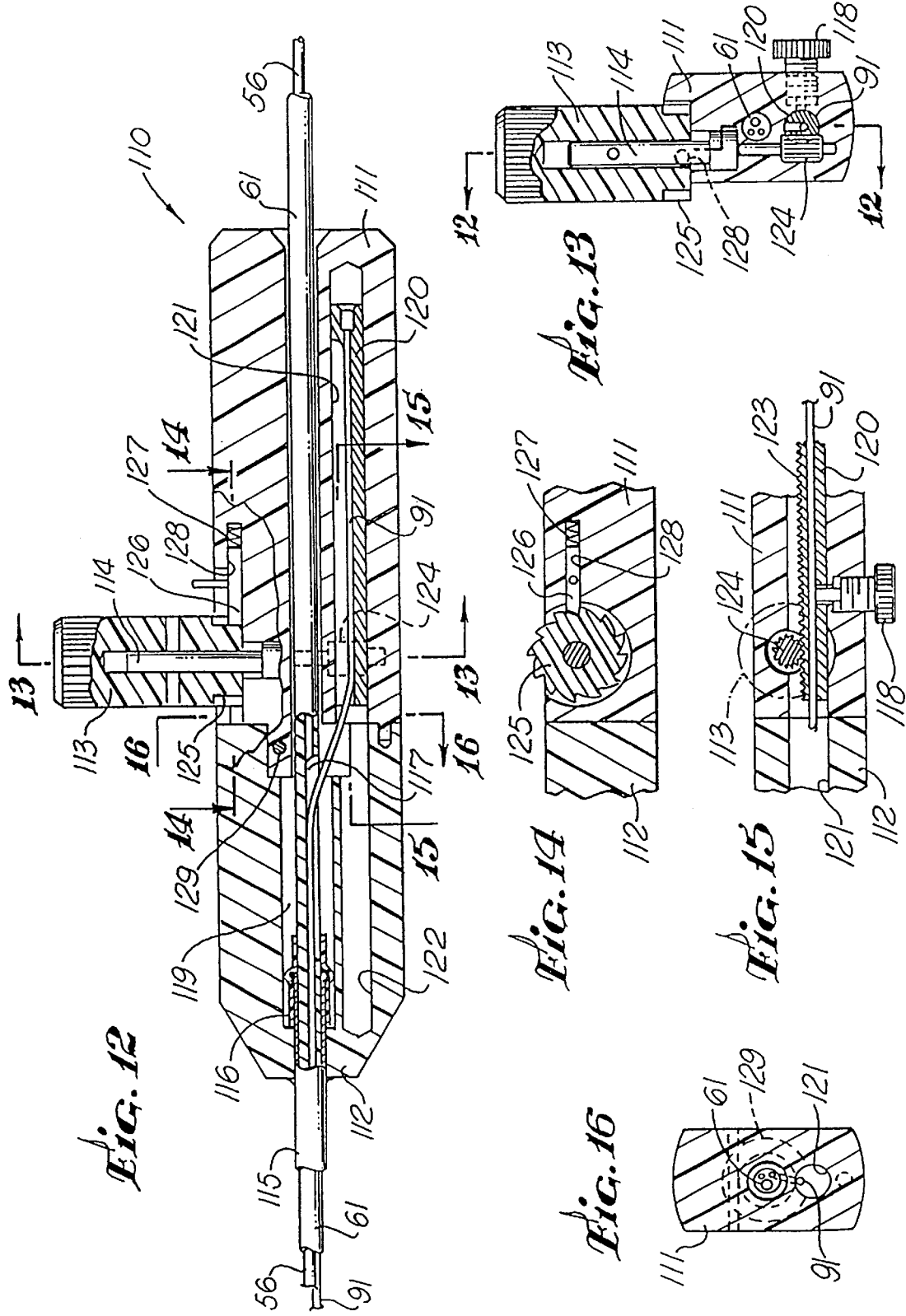

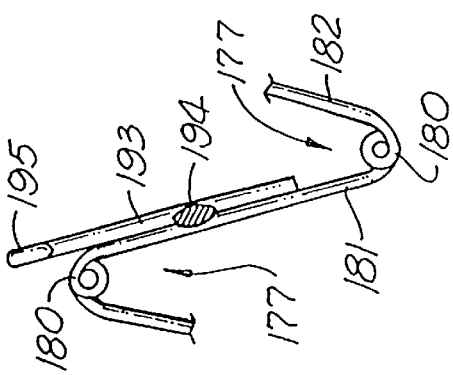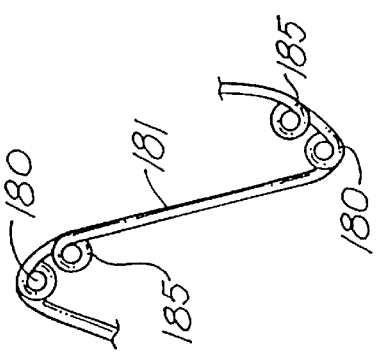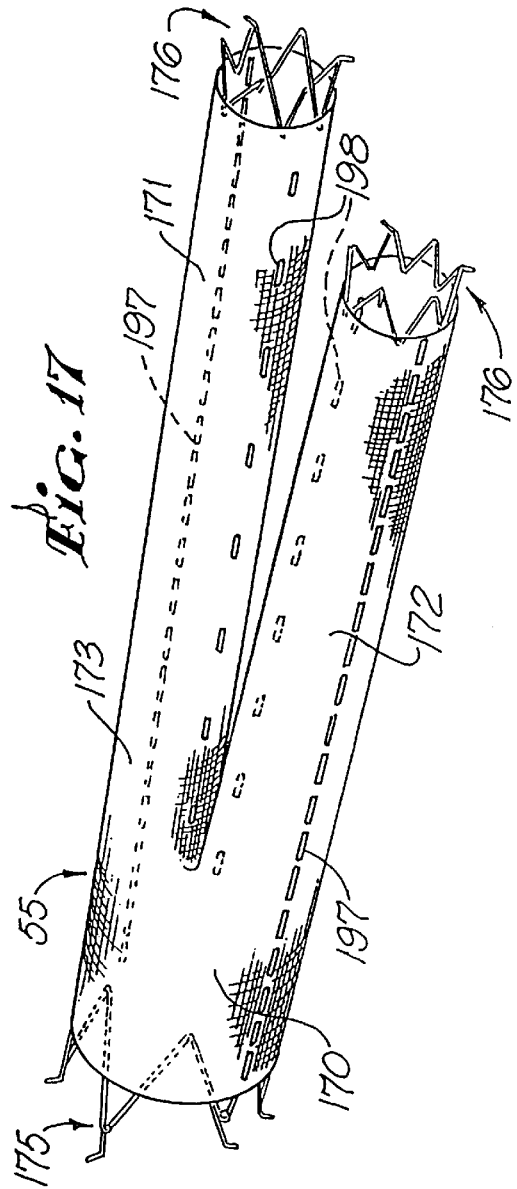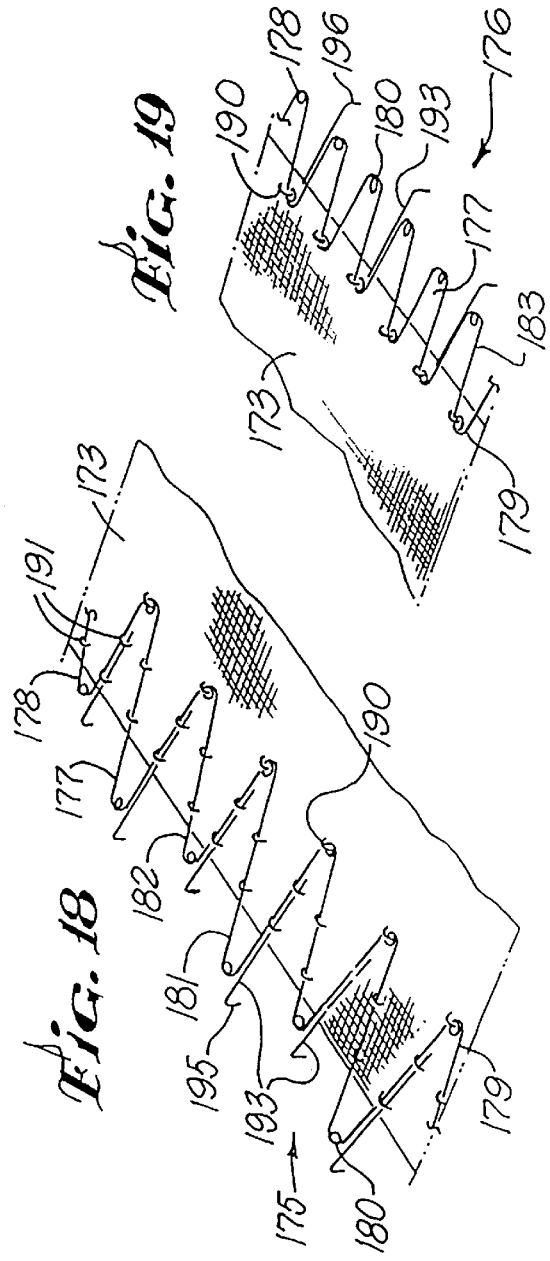

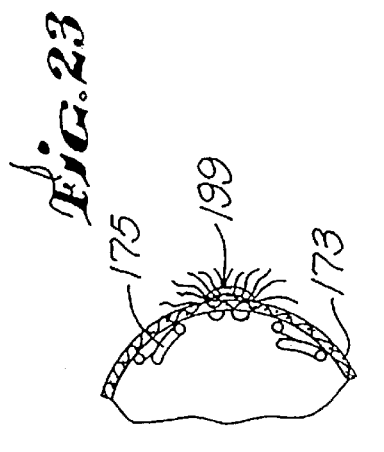
Fig. 23
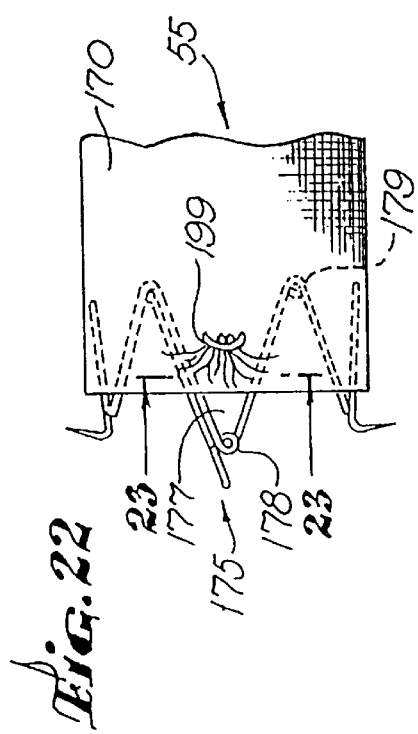
Fig. 22
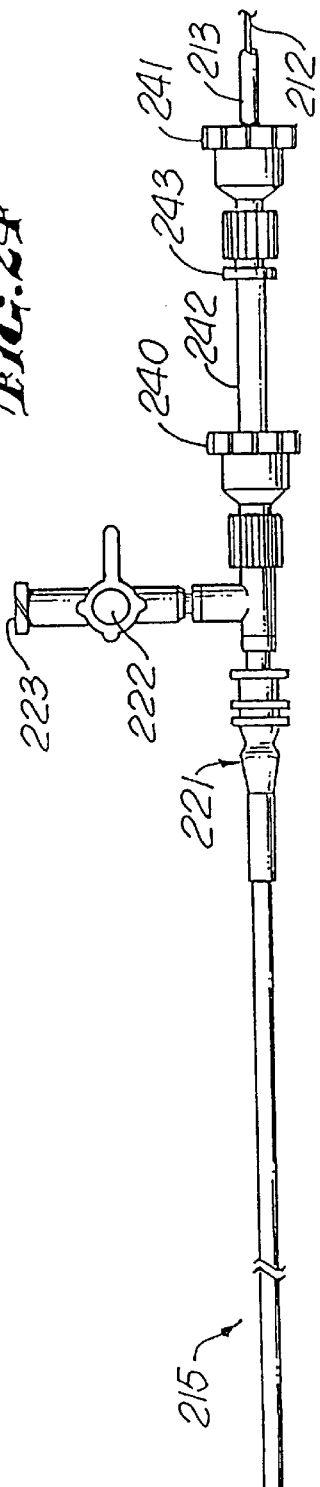
Fig. 24
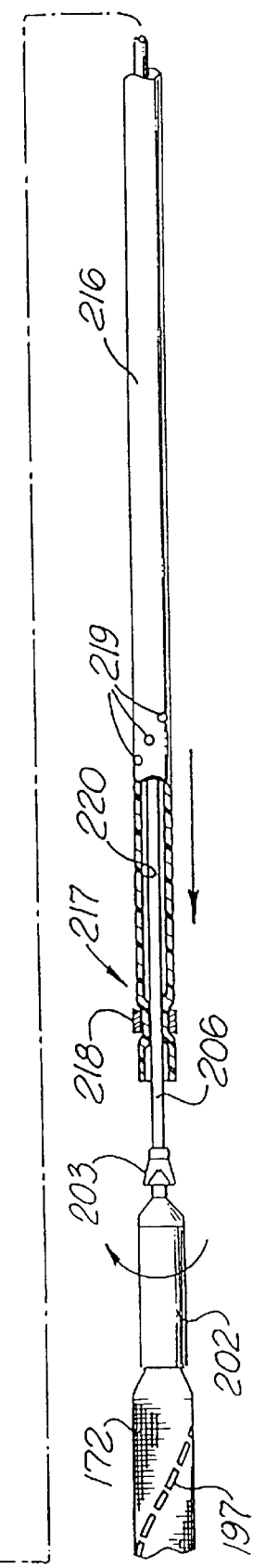

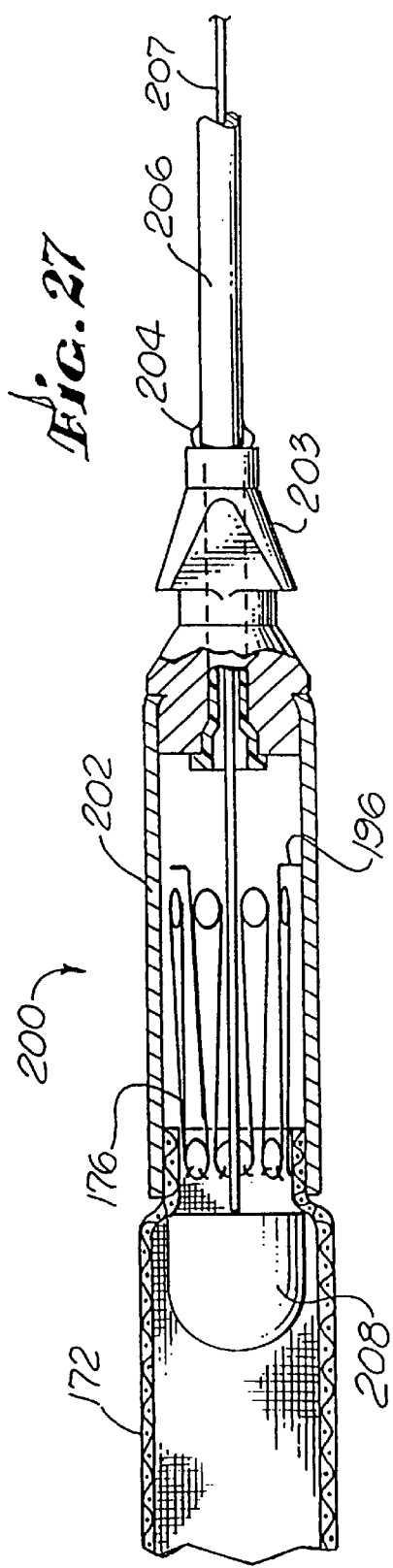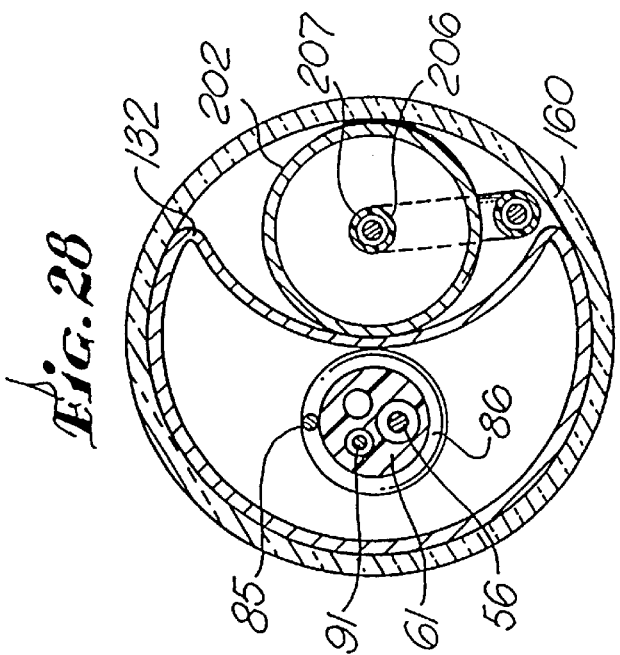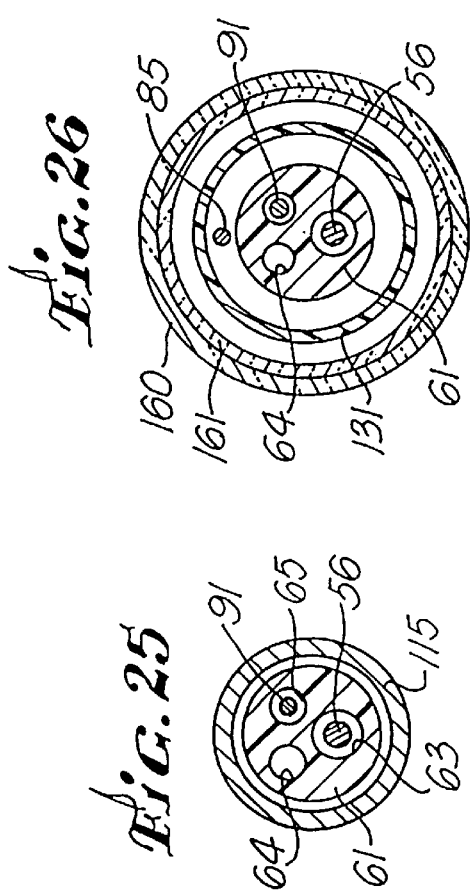

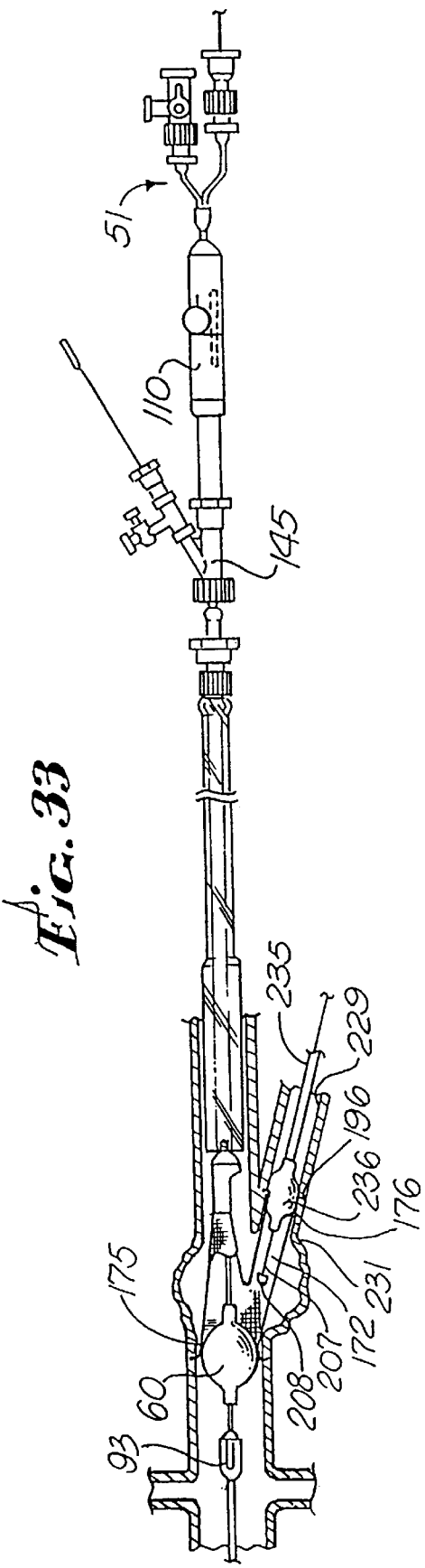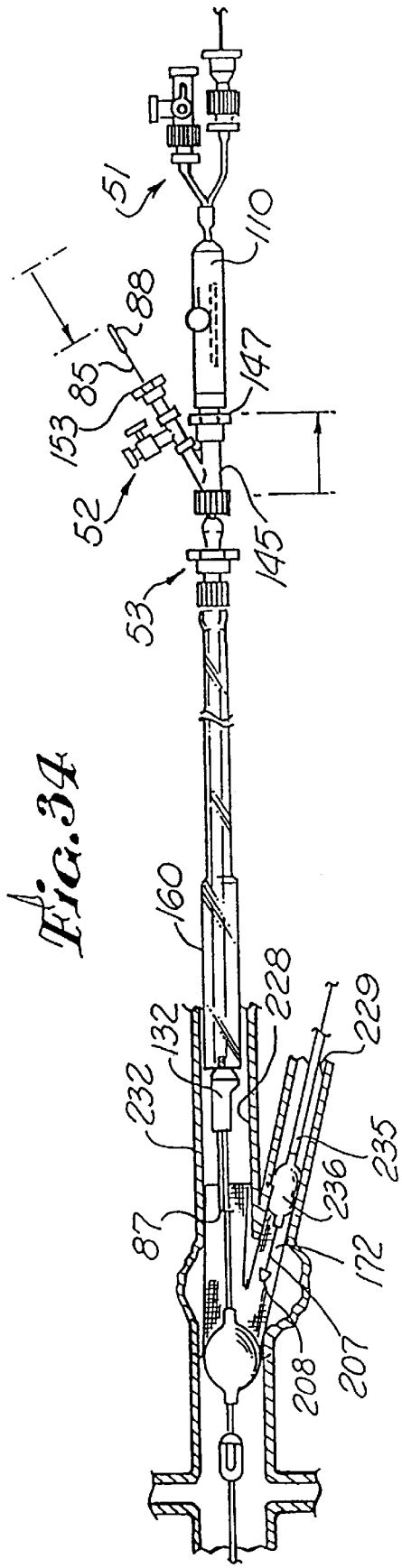

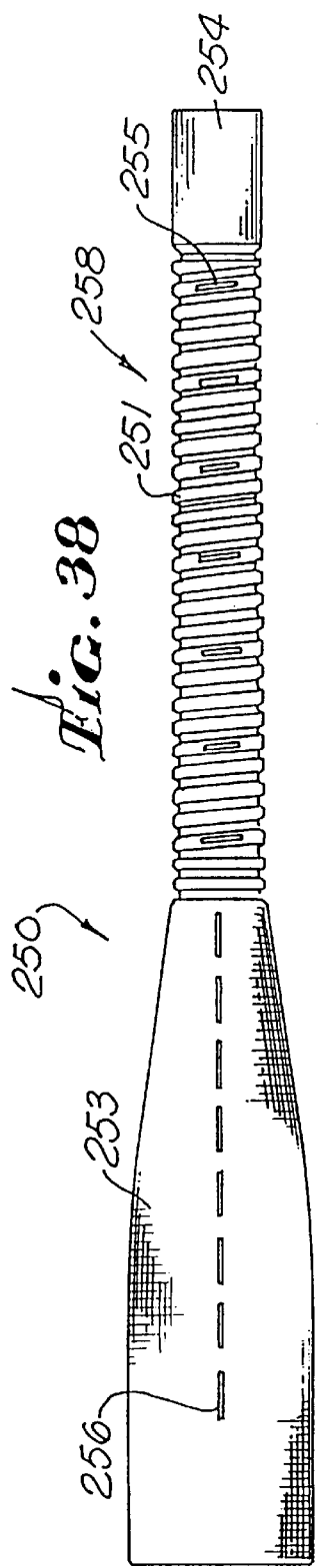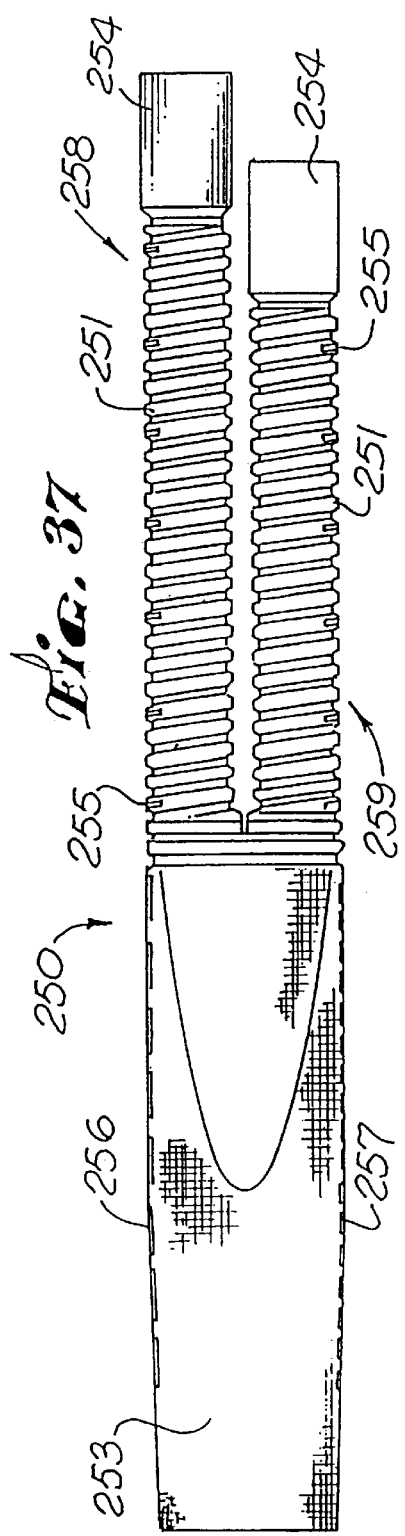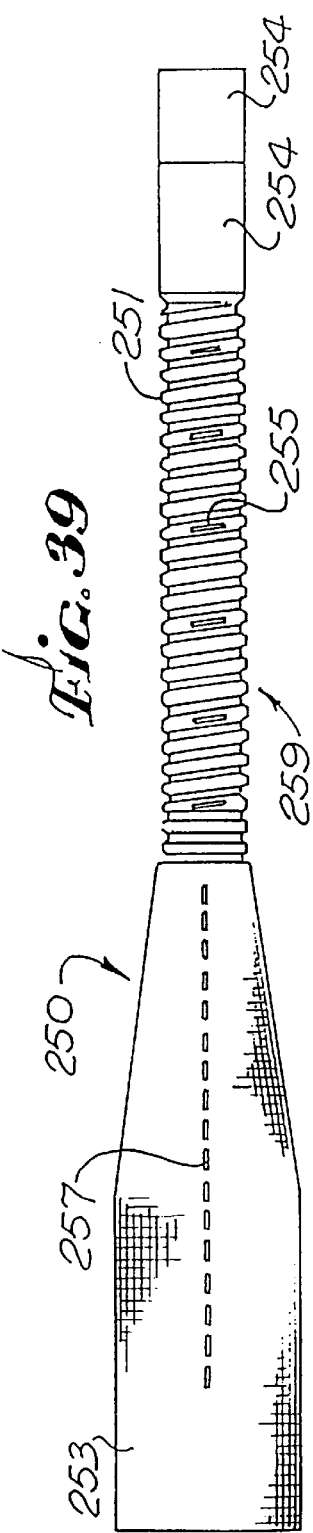

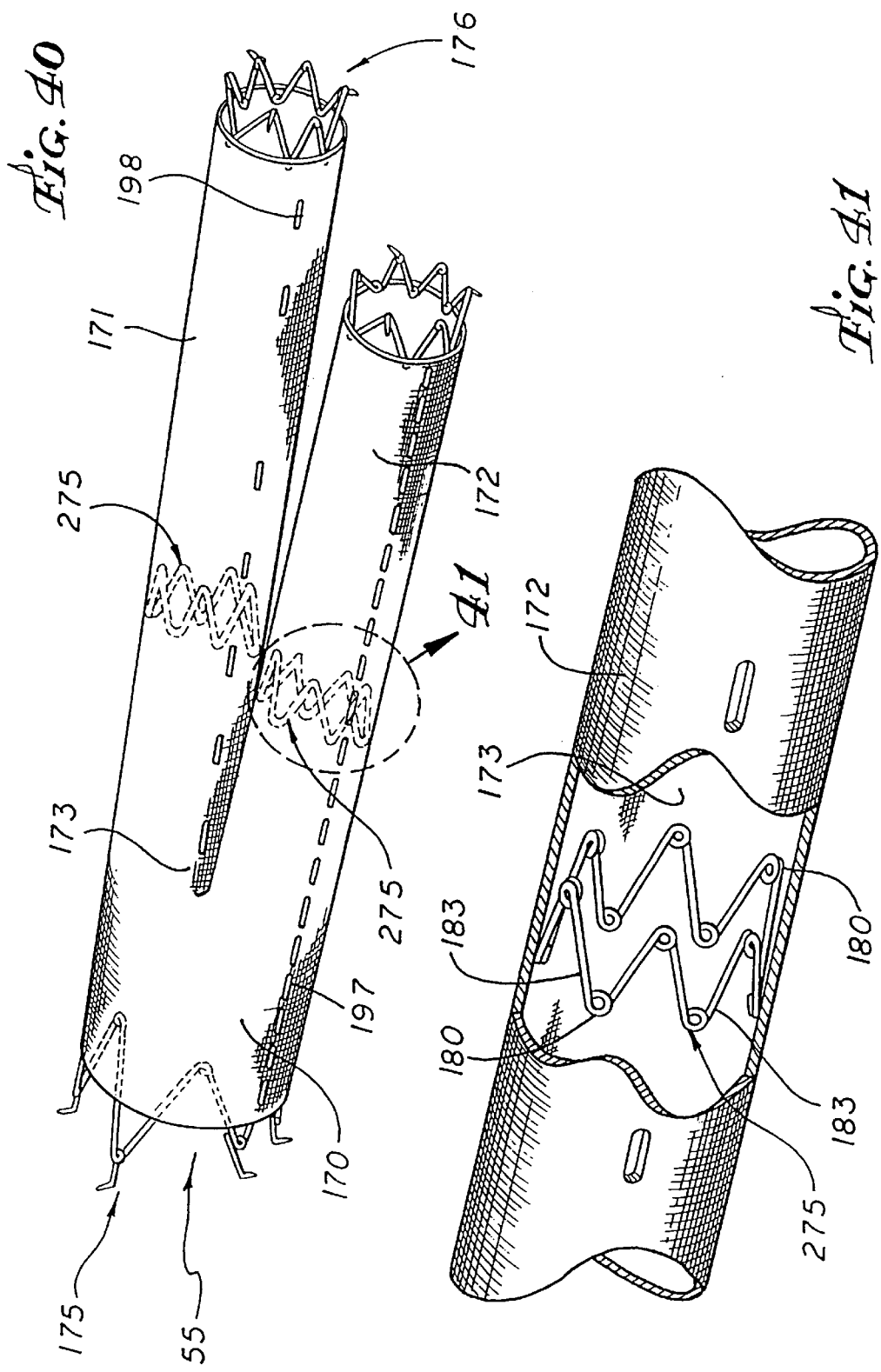

BIFURCATED MULTICAPSULE INTRALUMINAL GRAFTING SYSTEM AND METHOD

CROSS-REFERENCES TO RELATED APPLICATIONS

This is divisional of application Ser. No. 08/698,787, filed Aug. 16, 1996, now U.S. Pat. No. 5,769,885, which is a divisional of application Ser. No. 08/241,476, filed May 12, 1994, now U.S. Pat. No. 5,628,783.

BACKGROUND OF THE INVENTION

This invention relates to a system and method for emplacing a prosthesis and, more particularly, to a delivery catheter and method of use for placement within a corporeal lumen of a bifurcated graft having attachment systems.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and in turn may be life-threatening. In some cases, the damaged lumen is repairable only with the use of prosthesis such as an artificial vessel or graft.

For repair of vital vessels such as the aorta, surgical repair is significantly life-threatening. Surgical techniques known in the art involve major surgery in which a graft resembling the natural vessel is spliced into the diseased or obstructed section of the natural vessel. Known procedures include surgically bypassing the damaged or diseased portion of the vessel and inserting an artificial or donor graft attached to the native vessel by an anastomosis.

It is known within the art to provide a prosthesis for intraluminal repair of a vessel, such as an abdominal aorta having an aneurysm. The art has taught to provide a prosthesis positioned in a vessel then securing the prosthesis within the vessel with hooks or staples that are mechanically extended by the user. The early prior art devices were large in diameter, mechanically complex and in turn were susceptible to mechanical failure. Prior intraluminal grafting systems have embodied capsule catheters or balloon catheters, but were relatively stiff and of a relatively high profile. Similarly, the prior art systems were configured in such a way that the graft was relatively difficult to deploy in the correct position. In addition, prior systems having a capsule catheter assembly were usually configured such that the prosthesis was disposed within a unitary capsule.

In recent years, several devices have been developed to attempt to treat an aortic aneurysm through intraluminal repair. For example, U.S. Pat. No. 4,140,126 (Feb. 20, 1979), Choudhury, discloses a method and article for performing an aneurysm repair, wherein a prosthetic graft is utilized to replace the damaged segment of the blood vessel. A plurality of radially spaced anchoring pins are located adjacent each end of the graft and provide means for securing the graft to the wall of the vessel. An assembly is provided for moving the graft within the vessel and permanently anchoring the graft to the wall of the vessel.

U.S. Pat. No. 4,562,596 (Jan. 7, 1986), Kornberg, discloses a bifurcated aortic graft constructed for intraluminal insertion having a plurality of struts having angled hooks with barbs at their superior ends. An assembly for inserting the graft and implanting the hooks into the vessel lumen is also disclosed.

U.S. Pat. No. 4,787,899 (Nov. 29, 1988), Lazarus, discloses an intraluminal grafting system including a hollow graft having an attachment means located at one end of the graft. The system includes positioning means for moving the graft within the vessel, the positioning means having a capsule positioned at one end for covering the graft attachment means. The disclosed positioning means further includes an inflatable member for securing the attachment means within the lumen.

EPO Pub. No. 0 461 791 A1 (Dec. 18, 1991), Barone et al. discloses an aortic graft and apparatus for repairing an aneurysm. The disclosed system includes a tube graft secured within the aorta and an attachment means at each end of the graft. Intraluminal delivery is accomplished using a catheter having a balloon for expanding and securing the attachment means. The graft and attachment means are preferably enclosed by a sheath which covers the entire graft and attachment means.

U.S. Pat. No. 5,104,399 (Apr. 14, 1992), Lazarus, discloses an intraluminal grafting system including a tubular graft having attachment means positioned at both ends. The system includes a positioning means for transporting the graft through a vessel lumen and for deploying the graft within the lumen. The positioning means includes an inflatable member, a capsule and means for removing the graft from the capsule. The capsule is disclosed as a rigid cylindrical member covering the entire graft.

EPO Pub. No. 0 508 473 A2 (Oct. 14, 1992), Piplani et al., discloses an intraluminal grafting system including a catheter having a capsule formed of a helical wrap of metal ribbon. A bifurcated graft having attachment means is removably disposed within the capsule. Means is provided for moving the graft from the capsule, and an inflatable member is provided for securing the attachment means within a vessel lumen.

U.S. Pat. No. 5,256,150 (Oct. 26, 1993), Quiachon et al., discloses a large diameter sheath for use in introducing a catheter in the body of a patient. The sheath includes an flexible elongate sheath tube and a backflow adapter having a hemostatic valve secured to the proximal extremity of the sheath tube. The sheath may be used for introducing a large-diameter deployment catheter into a femoral artery of the patient.

U.S. Pat. No. 5,275,622 (Jan. 4, 1994), Lazarus et al., discloses an intraluminal grafting system including a catheter having a capsule formed of a helical wrap of metal ribbon. A tubular graft having attachment means at both ends is removably disposed within the capsule. Means is provided for moving the graft from the capsule, and an inflatable member is provided for securing the attachment means within a vessel lumen.

The foregoing patents and publications are incorporated herein by reference.

To provide consistency with the common usage of terms used in the medical surgical arts in the United States, the terms "proximal, distal, inferior and superior" are used with a certain regularity within the present specification. Proximal refers to parts of the system, such as catheters, capsules and wires, which are closest to the user and closest to the portion of the system outside or exterior of the patient. Distal refers to the point farthest from the user and typically most interior to the corporeal lumen. The term superior refers to a location situated above and is used herein in description of the graft and attachment system. Inferior refers to the point situated below and again is used herein with the graft and attachment system. Thus, for applications in the abdominal aorta which use a femoral approach, the superior end of the graft resides within the most distal portion of the delivery catheter. Likewise, the inferior end of the graft resides within the proximal capsule which is on the most distal portion of the capsule catheter.

The term "ipsilateral" typically refers to a vessel or part of a device which resides on the same side in which a device enters a lumen. For example, the ipsilateral tubular leg of a graft would be the tubular leg which resides in the iliac artery in which the capsule catheter enters the aorta. Similarly, the term "contralateral" refers to a vessel or device residing on the opposite side of which the main device enters the aorta. For example, the contralateral attachment system resides in the contralateral iliac artery which is on the opposite side of the aorta from which the capsule catheter enters the aorta.

SUMMARY OF THE INVENTION

The present invention comprises an intraluminal delivery system for securing a prosthesis within or between vessels or corporeal lumens of an animal, such as a human. The preferred embodiment of the placement system is configured for introducing a graft into a corporeal lumen and positioning the graft in the area of the aortic bifurcation. The delivery system includes a balloon catheter, a capsule catheter and a capsule jacket.

In general, it is an object of the present invention to provide an intraluminal grafting system and method which overcome the disadvantages of the prior art systems. The present invention comprises a system and method for implanting a prosthesis utilizing a catheter assembly having a multiplicity of capsules. The prosthesis comprises a wye shaped bifurcated graft having a self-expanding attachment system at each of its three orifices. Each attachment system is contained within its own compact capsule during deployment. The graft and capsules are deployed by a catheter assembly designed for traversing the femoral, iliac and aortic vessels of a human anatomy.

The present system has several advantages over prior art systems. For example, the over the wire configuration of the balloon catheter enables traversing the aneurysm with a guide wire. Using a guide wire in this manner minimizes the risk of dislodging thrombus in the aneurysm, since the delivery system follows the guide wire, thereby preventing the distal tip from perforating the vessel wall. In addition, using a guide wire allows for traversing more difficult anatomy. Also, the guide wire lumen may function as a through lumen for real time angiograms during the emplacement procedure or to insert intravascular probes such as intravascular ultrasound systems.

As another advantage, the smaller diameter of the capsule assemblies of the present invention permit use of the invention in a larger patient population because the variances in iliac vessel diameter. Similarly, the smaller device diameter relative to the iliac diameter may allow for easier navigation inside the corporeal lumen especially with more difficult anatomy. Likewise, the two capsule segments of the present invention permit a wider range of graft lengths than available with a single capsule design. The single capsule systems also require capsules slightly longer than the graft, which imposes certain manufacturing and deployment problems. Moreover, the shorter capsule segments provide a more flexible device, thereby allowing traversing more difficult anatomy.

In the preferred embodiment, the balloon catheter and the capsule catheter include capsule assemblies for retaining the attachment systems, including a distal capsule assembly for retaining the superior attachment system and a proximal capsule assembly for retaining the ipsilateral attachment system. Also included within the delivery system is a contralateral capsule assembly for retaining the contralateral attachment system. The capsule assemblies are movable relative to each other to allow the graft to be emplaced at the desired location in the corporeal lumen.

Preferably, the delivery system includes a balloon catheter having a multilumen hollow tube or shaft having a proximal end provided with an assembly for accepting a guide wire and with an assembly for inflating a balloon or similar inflatable member. The balloon catheter shaft is of sufficient length that the proximal end remains exterior the corporeal lumen while the distal end of the balloon catheter shaft may be positioned proximate the portion of the corporeal lumen to be repaired. The balloon catheter further has an assembly for inflating and deflating the balloon. In addition, the balloon catheter is coupled to a control assembly and a distal capsule for retaining and releasing the superior end of the graft. In the preferred embodiment, the control assembly includes a control wire and handle mechanism which provides movement of the distal capsule relative to the balloon catheter shaft.

The delivery system also includes a capsule catheter shaped and sized for positioning within the corporeal lumen. The capsule catheter comprises a hollow tube or shaft slidably mounted on the balloon catheter shaft, having a proximal end exterior the corporeal lumen for manipulation by the user. The capsule catheter includes a proximal (ipsilateral) capsule secured to the distal end of the capsule catheter shaft for retaining the ipsilateral attachment system. The delivery system is configured to provide relative movement between the proximal capsule of the capsule catheter and the distal capsule of the balloon catheter for removing the graft from the capsule assemblies and for subsequently urging the attachment systems into engagement with the wall of the corporeal lumen.

The placement assembly further includes a capsule jacket for providing a smooth transition between the parts of the balloon catheter and capsule catheter. The capsule jacket comprises a singled walled jacket or sheath covering the length of the prosthesis and a double walled section over the capsule catheter tubular member. The capsule jacket is configured coaxially with the balloon catheter and capsule catheter, having a proximal end exterior the corporeal lumen for manipulation by the user. The distal end of the capsule jacket is single walled and flares outwardly to a size which is slidably retained over the distal capsule when the placement assembly in deployed into the corporeal lumen. The capsule jacket distal tip has a radiopaque marker to facilitate positioning using fluoroscopy or x-ray techniques.

The present invention includes a bifurcated prosthesis or bifurcated graft for intraluminal placement in a fluid conducting corporeal lumen. For most applications the prosthesis is a hollow bifurcated graft of preselected cross-section and length. The bifurcated graft is deformable to conform substantially to the interior surface of the corporeal lumen or other body part to be repaired. Preferably, the bifurcated graft is made of a material suitable for permanent placement in the body such as polytetrafluroethylene or a polyester. The tubular legs and/or the main tubular member of the graft may be crimped to resist kinking during and after deployment. During emplacement, the superior and inferior ends of the bifurcated graft are positioned within the corporeal lumen and the graft is configured such that the graft traverses the diseased or damaged portion of the vessel. To anchor the graft to the wall of the corporeal lumen, attachment systems are secured to the superior and inferior ends of the graft.

The attachment systems for the ipsilateral and contralateral legs of the bifurcated graft are somewhat smaller than the attachment system used for the main tubular member. The attachment systems for the legs are sized for emplacement within the iliac arteries. During deployment, the ipsilateral leg attachment system resides within the proximal capsule and the contralateral leg attachment system resides within the contralateral capsule. The smaller profile of the leg attachment systems allow them to fit within the smaller capsules which are configured to fit together within the capsule jacket. Having the leg attachment system within each capsule allows the attachment systems to be secured to the tubular legs prior to deployment. In addition, the encapsulation prevents entanglement of the attachment systems.

The preferred attachment system has wall engaging members. The wall engaging members of the superior attachment system are angled toward the inferior end of the graft. Similarly, the wall engaging members of the inferior attachment system are angled slightly toward the superior end of the graft. The wall engaging members of both attachment system have sharp tips for engaging the corporeal lumen wall. The preferred attachment system are formed into a V-shaped lattice or framework. The frame of the attachment system allows for elastic radial deformation resulting in a spring-like effect when a compressed attachment system is allowed to expand as the graft is released from the capsule assembly. In addition, radiopaque markers are secured to the longitudinal axis of the graft to facilitate orientation of the graft using fluoroscopy or x-ray techniques.

The delivery system further includes a contralateral capsule system for retaining the contralateral leg of the bifurcated graft. The contralateral capsule system comprises a retaining capsule, guiding tube and a pull wire. A segment of the contralateral capsule guiding tube is configured to reside in the capsule jacket, and the remainder of the guiding tube and pull wire extend out of the distal end of the capsule jacket assembly. In addition, a radiopaque marker coil on the guiding tube coincides with the distal capsule of the balloon catheter assembly to facilitate orientation, i.e. relative twist, between the contralateral capsule assembly and the ipsilateral capsule assembly.

During deployment, the contralateral capsule resides within the capsule jacket and adjacent to the proximal capsule assembly. The contralateral capsule guiding tube is traversed through the contralateral iliac artery in a conventional manner such that the contralateral leg of the bifurcated graft can be secured within the contralateral iliac artery. The contralateral capsule is configured to retain the inferior attachment system secured to the contralateral tubular leg. Similarly, the contralateral guiding tube and capsule are configured such that the attachment system will remain within the capsule until such time when the clinician wishes to remove the capsule and free the attachment system within the contralateral iliac artery. The contralateral pull wire is disposed within the capsule jacket and along the distal capsule assembly and extends out the distal end of the capsule jacket.

Deployment of the graft comprises a series of steps which begins with introducing the main guide wire into the ipsilateral side of the corporeal lumen using well known surgical techniques. The contralateral guide wire and guiding tube are then inserted into the ipsilateral cutdown and are traversed through the contralateral cutdown using standard transfemoral techniques. Those techniques include use of a snare or guiding catheter traversed through the contralateral cutdown to assist in transferring the contralateral guide wire from the ipsilateral side of the corporeal lumen to the contralateral side. Next, as a single deployment catheter assembly, the balloon catheter, capsule catheter and capsule jacket are manipulated over the guide wire to position the capsules containing the bifurcated graft and attachment systems to a desired location within the corporeal lumen.

Once the graft is in the desired location, the capsule jacket is withdrawn to expose the entire graft and capsules containing the attachment systems. As the capsule jacket is retracted, tension is applied on the contralateral capsule assembly from the contralateral side of the corporeal lumen, thereby pulling the guiding tube out of the capsule jacket and into the contralateral lumen. The attachment systems are then simultaneously positioned at the desired locations. The distal capsule is then moved relative to the balloon catheter shaft and capsule catheter to expose the superior attachment system.

After the superior portion of the graft is removed from the distal capsule assembly, the inflatable member is moved to within the circumference of the superior attachment system and inflated to urge wall engaging members into the wall of the corporeal lumen. The contralateral capsule assembly is then withdrawn to expose the inferior attachment system of the contralateral tubular leg. An auxiliary balloon catheter is then positioned in the contralateral tubular leg to firmly secure the contralateral attachment system.

Once the contralateral tubular leg is secured, the proximal capsule assembly is withdrawn from the ipsilateral tubular leg, exposing the attachment system secured thereto. The deployment catheter is then moved to position the inflatable member proximate the ipsilateral inferior attachment system. The inflatable member is then expanded to seat the wall engaging members of the inferior attachment system. The deployment catheter is then removed from the corporeal lumen. An auxiliary balloon catheter is then positioned in the ipsilateral tubular leg to firmly secure the ipsilateral attachment system. All catheters and guide wires are then removed and the access to the corporeal lumens closed.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a top plan view of an intraluminal grafting apparatus and system incorporating the present invention.

FIG. 2 is a top plan view of a guide wire to be used with the endovascular grafting system of the present invention.

FIG. 3 is a top plan view of the balloon catheter and ipsilateral locking wire of the present invention.

FIG. 4 is a top plan view of the distal cap, control wire, hypotube and control wire handle assembly of the present invention.

FIG. 5 is a top plan view of the proximal capsule and capsule catheter assembly of the present invention.

FIG. 6 is a top plan view of the capsule jacket assembly of the present invention.

FIG. 7 is a top plan view of a bifurcated graft and contralateral capsule assembly of the present invention.

FIG. 8 is a partial cross-sectional view of the distal end of the balloon catheter, capsule catheter and capsule jacket assemblies taken along the line 8—8 of FIG. 1.

FIG. 9 is an enlarged perspective view showing an embodiment of the distal capsule, distal end of the control wire and distal cap insert.

FIG. 10 is an enlarged cross-sectional view of the distal capsule assembly of the balloon catheter.

FIG. 11 is a cross-sectional view taken along the line 11—11 of FIG. 10.

FIG. 12 is a partial cross-sectional view of the control wire and control-handle mechanism taken along the line 12—12 of FIG. 1.

FIG. 13 is a partial cross-sectional view taken along the line 13—13 of FIG. 12.

FIG. 14 is a cross-sectional view taken along the line 14—14 of FIG. 12.

FIG. 15 is a cross-sectional view taken along the line 15—15 of FIG. 12.

FIG. 16 is a cross-sectional view taken along the line 16—16 of FIG. 12.

FIG. 17 is an enlarged perspective view of the bifurcated graft and attachment systems of the present invention.

FIG. 18 is an top plan view showing a superior attachment system as sewn into the main tubular member of the graft.

FIG. 19 is an top plan view showing a inferior attachment system as sewn into a tubular leg of the graft.

FIG. 20 is an enlarged side plan view showing a superior attachment system

FIG. 21 is an enlarged side plan view showing an attachment system having a supplemental helix torsion spring at the apices.

FIG. 22 is a top plan view showing a piece of yarn sewn into the main tubular member of a graft adjacent to the vee of an attachment system.

FIG. 23 is a cross-sectional view taken along line 23—23 of FIG. 22. showing a piece of yarn sewn into the main tubular member of a graft adjacent to the vee of an attachment system.

FIG. 24 is a top plan view of a torque catheter disposed over the guiding tube of the contralateral capsule assembly of the present invention.

FIG. 25 is a cross-sectional view taken along the line 25—25 of FIG. 1.

FIG. 26 is a cross-sectional view taken along the line 26—26 of FIG. 1.

FIG. 27 is a partial cross-sectional view of the contralateral tubular leg and attachment system positioned in the contralateral capsule assembly.

FIG. 28 is a cross-sectional view taken along the line 28—28 of FIG. 8.

FIG. 33 is a partial cross-sectional view of the intraluminal grafting system, wherein the contralateral capsule has been removed from the inferior end of the contralateral tubular leg and an auxiliary balloon catheter has been positioned and inflated to seat the inferior attachment system.

FIG. 34 is a partial cross-sectional view of the intraluminal grafting system, wherein the proximal capsule has been removed from the inferior end of the ipsilateral tubular leg, releasing the ipsilateral inferior attachment system into the ipsilateral iliac artery.

FIG. 37 is an top plan view of a bifurcated graft of the present invention having crimped tubular legs.

FIG. 38 is a contralateral side view of the bifurcated graft of FIG. 37.

FIG. 39 is an ipsilateral side view of the bifurcated graft of FIG. 37.

FIG. 40 is an enlarged perspective view of the bifurcated graft, showing in hidden lines the additional attachment systems placed medial the ends of the tubular legs.

FIG. 41 is an enlarged cutaway view of a portion of one tubular leg of the bifurcated graft of FIG. 40, showing one additional attachment system.

DESCRIPTION OF THE PREFERRED EMBODIMENTS

Figure 29:
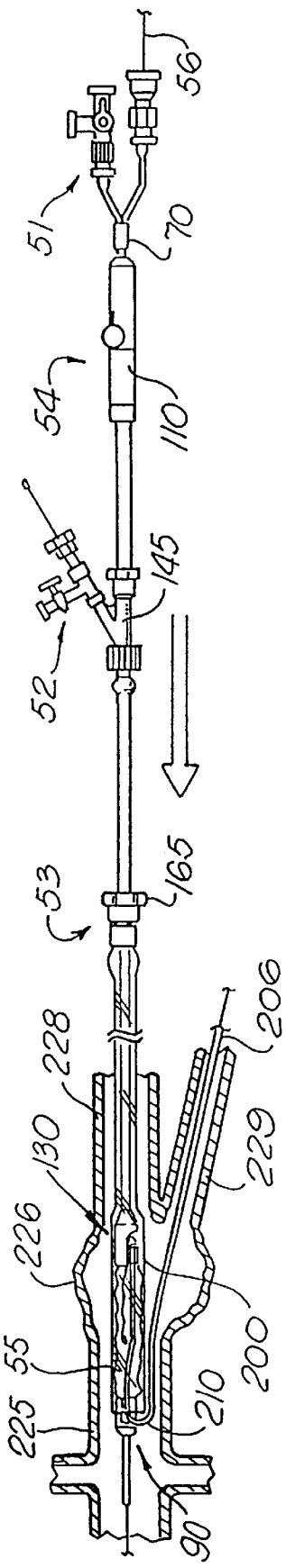
FIG. 29 is a partial cross-sectional view of the intraluminal grafting system shown positioned within the corporeal lumen.

As shown in the drawings and for purposes of illustration, the invention is embodied in an intraluminal grafting system of the type having a balloon catheter, a capsule catheter, and a protective sleeve or capsule jacket. One of the novel features of the present system is the use of a proximal capsule, a distal capsule and a contralateral capsule to cover the inferior and superior ends of a bifurcated graft to be implanted in a corporal lumen having a bifurcation. This feature provides the capability of deploying the inferior end of the graft before the superior end or visa versa. Another novel feature of the present invention is the use of a sleeve or capsule jacket to create a smooth transition between the proximal capsule, contralateral capsule, distal capsule and bifurcated graft. The uniqueness of the system is accentuated by the control wire and associated handle which provide relative movement between the distal capsule and the balloon catheter. Providing a contralateral capsule assembly enables including an attachment system in the contralateral tubular leg while avoiding tangling of the tubular legs during deployment.

In the present system, the graft is comprised of a bifurcated tubular prosthesis having superior and inferior extremities. The superior extremity of the graft comprises a main tubular member which bifurcates into two tubular legs which comprise the inferior extremity of the graft. For clarity, the two tubular legs are referred to herein as the ipsilateral tubular leg and the contralateral tubular leg. An attachment system is secured to the superior end of the main tubular member as well as to the inferior ends of each of the tubular legs. Each attachment system is provided with lumen piercing members which are covered during deployment by the proximal, distal and contralateral capsule assemblies. The balloon catheter, capsule catheter and capsule jacket are configured coaxially so that relative movement between them provides for deployment of the graft. The inflatable member of the balloon catheter is used to firmly implant the attachment systems, and thereby the graft, in the lumen.

In more detail, the intraluminal grafting system 50 is shown in FIGS. 1–7. As shown in FIG. 1, the system includes a balloon catheter assembly 51, which is coaxially disposed within capsule catheter assembly 52, which is coaxially disposed within capsule jacket assembly 53. The proximal capsule assembly 130, contralateral capsule assembly 200 and distal capsule assembly 90 are used to contain the bifurcated graft 55. A control wire assembly 54 is coaxially disposed within a lumen of the balloon catheter assembly and configured to move the distal capsule assembly in relation to the other system components. In the preferred embodiment, the system is used as an over-the-wire device, such that the balloon catheter is further configured with a lumen for a guide wire 56. It is contemplated, however, that the system can also be used with well known fixed wire delivery system configurations.

As shown in FIGS. 1 and 3, the intraluminal grafting system 50 also includes a balloon catheter assembly 51 which consists of an inflatable member or balloon 60 secured to a flexible elongate element or balloon catheter shaft 61. As shown in FIG. 25, the balloon catheter shaft is preferably configured with three lumens; however, the balloon catheter may be configured with a single, dual or similar multilumen shaft. A guide wire lumen 63 extends the length of the balloon catheter shaft. Similarly, a balloon inflation lumen 64 extends from the proximal end 70 of the balloon catheter to the inflatable member 60, wherein an inflation port 83, FIG. 8, is provided to allow inflation fluid to enter and exit the inflatable member. The third lumen 65 is provided for a control wire 91.

The flexible elongate element or balloon catheter shaft 61 is preferably formed of a material suitable for intraluminal use, such as irradiated polyethylene tubing. The three lumen balloon catheter shaft is preferably extruded to an outside diameter of 0.08 inches (2.03 mm). The guide wire lumen 63 has an inner diameter of 0.042 inches (1.07 mm). The inflation lumen 64 and the control wire lumen 65 have identical inner diameters of 0.022 inches (0.56 mm). However, the lumen inside diameter may range from 0.015 to 0.06 inches (0.381–1.52 mm) and the outside diameter may range from 0.035 to 0.1 inches (0.889–2.54 mm) for a multilumen balloon catheter shaft. The balloon catheter may vary in length to suit the application, for example, from fifty to one hundred-fifty centimeters.

Referring to FIG. 1, the proximal extremity 70 of the balloon catheter shaft 61 is secured to a splitting adapter 71 which splits the guide wire lumen 63 from inflation lumen 64. The side arm 72 of the adapter 71 has a stop cock 73 mounted at its proximal end which is movable between open and closed positions. The stop cock is provided with a Luer fitting 74 which is adapted to be secured to a syringe for injecting inflation fluid. The side arm 75 of the splitting adapter 71 is connected to female Luer fitting 77 for distal tip injection and to a Touhy Borst adapter 76 which is configured to removably and slidably receive the guide wire 56. A strain relief wire 78 is disposed in the control wire lumen 65 between the splitting adapter and the control handle assembly 110.

The inflatable member or balloon 60 is preferably secured twelve centimeters from the distal extremity 80 of the balloon catheter shaft 61. The balloon is positioned proximal of the distal capsule assembly 90 and the superior end of the graft 55. For shorter grafts of four to seven centimeters in length, the inflatable member may be positioned distal of the distal capsule assembly. The balloon is formed of suitable material such as polyethylene. The polyethylene utilized for the balloon is irradiated to achieve an appropriate balloon size. For larger diameter balloons, higher tensile strength materials like polyethyleneterephthalate (PET) is desirable because thinner walls, hence a lower profile, can be achieved.

The balloon can vary in diameter from twelve to forty-five millimeters in diameter and can have a wall thickness ranging from 0.001 to 0.005 inches (0.0254–0.127 mm). The preferred balloon made in accordance with the present invention has an outside diameter of twenty-four millimeters, a diameter equal to the inner diameter of the graft, and has a wall thickness of approximately 0.003 inches (0.076 mm). In addition, the balloon is pleated along its axis for a low profile which facilitates its introduction into a corporeal lumen of a patient as hereinafter described. Further, the deflated balloon is heated to provide it with a memory of its low profile configuration.

The balloon catheter shaft 61 is provided with an inflation lumen 64 which is in fluid communication with the inflation port 74. The inflation lumen is used to inflate and deflate the balloon 60 by introducing and withdrawing a gas or liquid through the inflation port. The balloon is secured approximately twelve centimeters from the distal extremity 80 of the balloon catheter shaft. The balloon proximal stem 81 and balloon distal stem 82 are heat sealed to the balloon catheter shaft to form a fluid tight seal. The length of the proximal stem may vary from 0.5 to 1.0 centimeter.

The balloon catheter shaft 61 has an inflation port 83 located approximately ten millimeters distal the balloon proximal stem 81. In addition, a radiopaque marker 84 is embedded in the balloon catheter shaft approximately two millimeters distal the balloon inflation port. Preferably, the radiopaque marker is a platinum or tungsten coil one centimeter long with an outer diameter of 0.02 inches (0.508 mm) and is located proximate the center of the balloon 60. Also, a strain relief or support wire 97 is disposed in the inflation lumen 64 between the distal end 80 of the balloon catheter shaft and the balloon distal stem 82.

It should be appreciated that although a separate inflatable member has been described in the drawing, an integral coaxial inflatable member may be provided which is formed of the same tubing from which the balloon catheter shaft is made. This can be readily accomplished, as is well known to those skilled in the art, by using an additional radiation dose for the balloon region of the shaft.

As shown in FIGS. 1, 3 and 8, the ipsilateral locking wire 85 runs parallel to the balloon catheter 61 within the capsule catheter assembly 52. The distal end of the ipsilateral locking wire may be configured with a proximal locking ring 86 and a distal locking ring 87 secured approximately twelve millimeters apart. The radiopaque locking rings are disposed within the distal end of the capsule catheter assembly during deployment and secure the ipsilateral attachment system of the bifurcated graft 55 within the distal end of the capsule catheter assembly. In the preferred embodiment, however, only the distal locking ring is used.

The proximal end of the ipsilateral locking wire 85 is disposed in the proximal end of the capsule catheter assembly 52. The proximal extremity of the locking wire is configured with a segment of stainless steel hypotube approximately sixty millimeters long to form a handle 88. The ipsilateral locking wire handle is used to laterally move the radiopaque proximal and distal locking rings 86 and 87 which engage the ipsilateral attachment system of the ipsilateral tubular leg of the bifurcated graft 55. Movement of the handle in relation to the capsule catheter assembly permits removal of the ipsilateral attachment system from the capsule catheter assembly.

The balloon 60 can also be observed under x-rays if carbon dioxide is used as the inflation medium, because the blood in the patient's vessel is more opaque than the gas used for inflating the balloon. In addition, increased visibility of the balloon can be obtained by inflating the balloon with a diluted radiopaque contrast solution. In addition, radiopaque bands of a suitable material such as platinum or a platinum-tungsten alloy can be placed on the proximal and distal balloon stems 81 and 82 to aid in ascertaining the position of the balloon. Similarly, radiopaque rods may be inserted in the balloon inflation lumen.

The intraluminal grafting apparatus also includes a control wire assembly 54, which is shown in FIGS. 1 and 4. The distal end of the control wire assembly consists of a distal capsule assembly 90. As shown in more detail in FIGS. 9–11, the distal capsule assembly comprises a control wire 91 disposed within a cylindrical distal cap 92 and distal cap insert 96 disposed within the distal cap. The distal cap insert is secured to the distal cap by means of an adhesive, solvent bonding, ultrasonic welding or by heat shrinking. A hollow distal capsule 93 is secured to the distal cap and coaxially surrounds the control wire and balloon catheter shaft 61.

The control wire 91 is slidably disposed in the control wire lumen 65. A longitudinal slot 94 is cut out of the balloon catheter shaft 61 to expose the control wire lumen and the control wire. To secure the control wire within the distal capsule assembly 90, the control wire is threaded through an opening 98 in the distal cap insert 96. The control wire is formed in a U-shaped bend over the opening in the distal cap insert and is configured to slide within the slot and the control wire lumen of the balloon catheter shaft. The distal end 95 of the control wire resides in the portion of the control wire lumen beyond the distal end of the slot.

The configuration shown in FIGS. 9–11 allows the distal cap assembly to move axially along the balloon catheter shaft. The U-shaped bend of the control wire through the distal cap insert, however, prevents the distal cap assembly from rotating in relation to the balloon catheter shaft. As described above, the distal cap insert is firmly secured within the distal cap 92. To prevent rotation of the distal cap, a three centimeter length of the control wire extends distal of the distal cap and is slidably disposed in the control wire lumen 65 of the balloon catheter shaft 61.

As shown in FIG. 10, balloon catheter proximal cap 100 is secured to the balloon catheter shaft 61 at a position distal the balloon distal stem 82 and proximal the aperture 94. The proximal cap is secured to the balloon catheter shaft by adhesive and by means of two retaining bumps 101 and 102. These retaining bumps secure the proximal cap in place, limiting its movement. Such a configuration provides a rounded, atramatic transition from edge 103 of the distal capsule 93 resting on the top surface of the proximal cap when the distal capsule is its most distal position.

As the control wire 91 is moved in a longitudinal manner, the distal end 95 of the control wire, the distal cap insert 96, the distal cap 92 and the distal capsule 93 each move as a single assembly. The proximal edge 103 of the distal capsule is rolled, curved or crimped inward, or deburred and smoothened so that the proximal cap will provide a smooth transition along the distal capsule assembly 90 when the distal capsule is advanced. The distal movement of the distal capsule is limited by a third retaining bump 99 positioned approximately 2.5 centimeters distal the balloon distal stem 82. The third retaining bump limits the amount of distal movement of the distal capsule assembly so that when the assembly is fully advanced the proximal edge of the distal capsule coincides with the top surface of the proximal cap 100.

Referring to FIG. 9, the distal cap 92 may be formed from polycarbonate or other suitable material for insertion through the body lumen. The distal cap is formed with a bore 104 of approximately the same diameter as the outer diameter of balloon catheter shaft 61. Similarly, the distal cap insert 96 may be formed of the same material as the distal cap, wherein the distal cap insert is provided with a bore 105 for receiving the balloon catheter shaft. The distal cap is further provided with a recess 106 or other means for receiving the distal end of the distal capsule 93. The distal capsule is preferably formed of stainless steel, but may be formed of other suitable biocompatible material, such as a nickel titanium.

Each of the pieces of the distal capsule assembly 90 fit snugly in a coaxial configuration. The distal cap recess 106 is angled to allow crimping of the distal capsule 93 to the distal cap 92. In addition, the distal capsule is configured with a longitudinal semicircular recess 107 in which the guiding tube 206 resides during deployment. Similarly, the distal cap is configured with a cutout slot 108 and the distal cap insert 96 is configured with a longitudinal recess 109 to accept the recess in the distal capsule. The distal cap cutout inhibits the relative rotation between the distal capsule proximal cap 100 and ultimately the balloon capsule shaft 61.

The proximal cap 100 is configured with two concentric alignment holes 140 in its walls. The alignment holes may range from 1.5 to 2.5 millimeters (preferably 2.5) in diameter and are formed 0.5 millimeters from the distal edge of the proximal cap. The alignment holes, which are not radiopaque, are used under fluoroscopy during the deployment of the graft 55 to indicate the optimal orientation of the main tubular member 170 as the superior attachment system 175 is released from the distal capsule assembly 90.

The outside diameter of the distal cap 92 and capsule 93 may range from 4 to 9 millimeters and is preferably 0.282 inches (7.16 mm) in outer diameter and 0.276 inches (7.01 mm) inner diameter. Similarly, the balloon catheter proximal cap 100 is comprised of stainless steel and has an outside diameter slightly less that of the distal capsule so as to provide a smooth transition. The proximal end of the proximal cap is preferably rounded to minimize trauma in the vessel and to facilitate balloon retraction into the bifurcated graft 55 during the emplacement process. The distal capsule may range in length from one to five centimeters, and preferably is 3.5 centimeters long so as to adequately retain the superior extremity of the main tubular member of the graft.

As shown in FIGS. 12–16, a handle assembly 110 is secured to the proximal end of the control wire 91. The handle assembly comprises a proximal body 111, a distal body 112, a control knob 113 with rotating shaft 114 and a hypotube 115. The two handle body parts have a central bore 119 for receiving the balloon catheter shaft 61. A retaining pin 129 may be used to secure the two pieces of the handle body together.

The hypotube 115 is coaxially disposed over the balloon catheter shaft 61 and extends distally from the central bore 119 in the distal handle body 112. The proximal end of the hypotube is secured to the balloon catheter shaft approximately one centimeter proximal from the distal end of the distal handle body by means of a polyethylene sealing tube 116 which is heat shrunk over the proximal end of the hypotube. An adhesive may be used to fix the distal handle body to the hypotube.

Hypotube 115 consists of a rigid thin wall tube formed of a suitable material such as stainless steel. The hypotube has a length of about 55 centimeters and has an outside diameter of 0.095 inches (2.41 mm) and an inside diameter of 0.087 inches (2.21 mm). When a crimped graft 55 is used, the hypotube may have marker bands (not shown) at predetermined positions distal of the control handle body 112. A crimped graft is loaded into the capsule assemblies in its most stretched configuration. After the capsule jacket assembly 53 is retracted, then adjustments need to be made to the position of the hypotube relative to the capsule catheter assembly 52 for the graft to resume its crimped length under physiological pressure. The marker bands facilitate the correct positioning of the inferior end of the graft.

Referring to FIG. 12, the control wire 91 resides in a balloon catheter lumen 65 and extends from the distal capsule assembly 90 to an aperture 117 located in the lumen just proximal of the proximal end of the hypotube 115. The control wire preferably consists of an elongate solid flexible stainless steel wire having a lubricating coating, such as fluorinated ethylene-propylene (FEP). The coated control wire is about 0.02 inches (0.508 mm) in diameter, providing sufficient strength to move the distal capsule assembly without buckling or kinking.

The proximal end of the control wire 91 is disposed within a retaining rack 120, approximately six centimeters long and having a central bore to secure the control wire. The retaining racks's proximal end is slidably disposed within a longitudinal guiding slot 121 in the proximal handle 111. Similarly, the retaining rack's distal end is slidably disposed within an longitudinal slot 122 in the distal handle body 112.

The retaining rack 120 is configured with teeth 123 along a longitudinal edge which engage a pinion or gear 124. The pinion is attached to a lower end of the rotating shaft 114. The upper end of the rotating shaft is secured within the control knob 113 such that rotation of the control knob rotates the gear and in turn moves the retaining rack longitudinally within the guiding slots. Longitudinal movement of the retaining rack causes longitudinal movement of the proximal end of the control wire 91, causing like longitudinal movement of the distal end 95 of the control wire and of the distal capsule 93. As shown in FIGS. 13 and 15, a locking screw 118 is configured to fix the retaining rack in place. The locking screw ensures that the control wire and distal capsule will not move even if torque is applied to the control knob.

At the base of the control knob 113 is a locking gear 125 which has curved teeth. The curved teeth engage a locking pin 126 biased by a locking spring 127 disposed within a recess 128 in the upper surface of the proximal body 111 of the control handle 110. The configuration of the curved teeth allows the control knob to turn in only one direction while the locking pin engages the locking gear. When the locking pin is moved to compress the locking spring, then the control knob may be turned in either direction. The locking gear is preferably molded as part of a plastic control knob, but may be a separate mechanism secured to the base of the control knob.

As shown in FIGS. 1 and 5, the capsule catheter assembly 52 consists of a proximal (ipsilateral) capsule catheter assembly 130 secured to the distal end of a flexible elongate tubular member 131 formed of a suitable plastic material such as polyether block amide available under the trademark "PEBAX", available from Atochem Polymers, Glen Rock, N.J. The capsule catheter elongate tubular member is of a suitable length as, for example, forty to one hundred centimeters and preferably approximately seventy-five centimeters for the abdominal aortic-iliac arteries and approximately ninety-five centimeters for the thoracic aortic artery. The elongate tubular member has a preferred outside diameter of 0.187 inches (4.75 mm) and an inside diameter of 0.125 inches (3.175 mm). The elongate tubular member can be produced in a certain color such as blue. To render the elongate tubular member radiopaque under x-rays, its material of construction may contain a radiopaque material, such as twenty percent by weight of bismuth subcarbonate or barium sulfate. The elongate tubular member may have markings or bands distal of the wye adapter 145 at predetermined positions to indicate capsule jacket retraction and locking points.

The proximal catheter assembly 130 includes a proximal (ipsilateral) capsule 132 mounted on the distal extremity of the capsule catheter elongate tubular member 131. The elongate tubular member also serves as a shaft for advancing the proximal capsule, as hereinafter described. Thus, the elongate tubular member should have a diameter which is less than that of the proximal capsule, preferably having an outside diameter ranging from three to seven millimeters.

The proximal capsule 132 is configured to approximately match the size of the distal capsule assembly 90. The proximal capsule is somewhat oval in shape, having opposite concave and convex outer surfaces, resembling a crescent moon (FIG. 28). The proximal capsule has a preferred diameter ranging from four to nine millimeters, which may be configured to accommodate different size grafts. The proximal capsule is preferably made of stainless steel or similar impermeable and rigid, or semi-flexible material.

Referring to FIG. 8, the proximal (ipsilateral) capsule 132 is secured to the distal extremity of the elongate tubular member 131 by means of a capsule adapter assembly 133. The capsule adapter assembly comprises a housing 134 and an inner sleeve 135, which may be constructed from polycarbonate. The capsule adapter housing distal extremity 136 is secured in the proximal extremity of the capsule, for example, by crimping, by using a press fit swaging or an adhesive such as a cyanoacrylate ester. The capsule adapter housing distal extremity may be angled to facilitate securing the housing to the proximal capsule.

The proximal extremity of the capsule adapter housing 134 is secured to the distal extremity of the elongate tubular member 131 by means of an cyanoacrylate ester adhesive, or other suitable means. To facilitate a mechanical lock, the elongate tubular member distal extremity is molded to form a flange 137, wherein the capsule adapter housing is configured so as to close around the flange. The capsule adapter housing is further provided with a recess for receiving the capsule adapter inner sleeve 135. The inner sleeve is provided with a bore of a suitable diameter so as to allow the balloon catheter shaft 61 to reside therein. The inner sleeve may further be provided with radiopaque marker rods or flat ribbons 138 for detection of the capsule adapter assembly 130 during fluoroscopy. In the preferred embodiment, the flange is bonded to the capsule adapter 134 without using the inner sleeve.

A female Luer adapter with barb (not shown) is secured to the proximal extremity of the elongate tubular member 131 of the capsule catheter assembly 52 and a wye adapter 145 is secured to the female Luer adapter. The central arm 146 of the wye adapter is connected to a Touhy Borst adapter 147 which tightens around the hypotube 115 disposed in the central arm of the wye adapter. The side arm 148 of the wye adapter has a stop cock 149 mounted therein which is movable between open and closed positions. The stop cock is provided with a Luer fitting 150 which is configured to accept a syringe for injecting a dye or other fluid. The side arm is also configured with a Touhy Borst adapter 153 which tightens around the ipsilateral locking wire 85 or preferably with a collet lock mechanism and O-ring (not shown) which tightens around the ipsilateral locking wire for hemostasis. The ipsilateral locking wire is disposed in the capsule catheter assembly 52 through the side arm of the wye adapter and between the balloon catheter shaft 61 and the elongate tubular member 131.

Air may be purged from the capsule jacket assembly 53 by injecting fluid through the Luer fitting 150 in the side arm 148. The injection fluid and air will exit purge ports 151 and 152, thereby filling the capsule jacket assembly with injection fluid. The Luer fitting also may be attached to a saline drip line during the operative procedure and may be used for contrast hand syringe injections for real time angiograms. In addition, a length of polyethylene tubing 154 is adhered over and distal the proximal end of the elongate tubular member 131 and over the distal end of the wye adapter 145 or female Luer adapter to provide strain relief.

Referring to FIGS. 1, 6 and 8, the capsule jacket assembly 53 is slidably disposed coaxially over the capsule catheter assembly 52 and the balloon catheter assembly 51 (FIG. 26). The capsule jacket assembly is comprised of a main sheath 160, a support sheath 161, a locking connector 162 and a sheath adapter 164. The main and support sheaths are coaxial from their proximal end, to a point approximately twelve to twenty-five centimeters from the distal end 163 of the main sheath, depending on the length of the graft. At the distal extremity of the support sheath, the main sheath flares to a larger diameter covering the proximal capsule 132, the contralateral capsule 202, the bifurcated graft 55 and the distal capsule 93. The diameter of the main sheath is about 0.263 inches (6.68 mm) at its proximal end and about 0.3 inches (7.62 mm) at the distal end 163.

The proximal ends of the sheaths 160 and 161 may be secured to the sheath adapter 164 of the locking connector by mechanical means and by adhesive. In addition, a length of polyethylene tubing 167 is adhered over the sheath adapter and over the proximal ends of the sheaths to secure the parts from separating. The distal end of the main sheath of the capsule jacket is provided with radiopaque marker 166 about five millimeters in longitudinal length.

When the capsule jacket assembly 53 is in its most distal position, the distal end 163 of the capsule jacket main sheath 160 extends to cover at least a portion of the distal capsule assembly 90. Similarly, the capsule jacket locking connector 162 is thereby positioned just proximal the proximal capsule catheter purge port 151. Prior to insertion into the lumen, the locking ring 165 is turned down to hold the capsule jacket assembly firmly in place, thereby maintaining a smooth transition surface along the length of the intraluminal grafting system 50. When the locking ring is released, the capsule jacket assembly may be moved to a furthermost proximal position, wherein at least a portion of the proximal capsule catheter assembly is exposed. Thus, the locking connector is positioned just distal the capsule catheter wye adapter 145. The locking ring may be tightened at any intermediate position to firmly secure the capsule jacket assembly at the desired location. In addition, a radiopaque marker 166 is provided at the distal end of the main sheath to facilitate proper linear positioning of the main sheath.

As shown in FIGS. 1, 7 and 17, the intraluminal grafting apparatus 50 also includes an expandable, collapsible and flexible intraluminal vascular bifurcated prosthesis or graft 55 for implanting in a body vessel or corporeal lumen. Referring to FIG. 17, the graft consists of a deformable main tubular member 170 which bifurcates into an ipsilateral tubular leg 171 and a contralateral tubular leg 172. The main tubular member and tubular legs each are formed of a cylindrical or continuous wall 173 allowing fluid communication between the superior and inferior ends of the bifurcated graft.

The main tubular member 170 may have a length in the range of two to ten centimeters, where 7.5 centimeters is suitable for most patients. The main tubular member may have a maximum expandable diameter ranging from fourteen to forty millimeters and a minimum diameter in a collapsed condition of 0.175 to 0.3 inches (4.44–7.62 mm). The tubular legs 171 and 172 may have a length in the range of three to ten centimeters, where five centimeters is suitable for most patients. The graft wall 173 can be woven of any surgical implantable material such as polytetrafluroethylene or a polyester fiber made from polyethylene terephthalate (PET), such as "DACRON" (Type 56). One material found to be satisfactory is "DEBAKEY" soft woven "DACRON" vascular prosthesis (uncrimped) sold by C. R. Bard of Billerica, Mass. In order to prevent unraveling of the woven material at the ends, the ends can be melted with heat to provide a small melted bead of material on each end.

FIGS. 37–39 discloses an alternate embodiment of a bifurcated graft 250. Crimps 251 are configured in the ipsilateral and contralateral tubular legs 252 to resist kinking of the graft when deployed in a corporeal lumen. The crimps begin just superior to the bifurcation from the main tubular member 253 and are evenly spaced along the tubular leg. The crimps discontinue approximately five millimeters superior the inferior ends 254 of the tubular legs so as to provide sufficient space for the inferior attachment systems (not shown) to be sewn into the inferior ends of the tubular legs. The crimps may be annularly or helically spaced along the tubular leg. Similarly, crimps may also be provided in the main tubular member of the graft.

Although a standard size crimp may be used, it is preferred to make the crimps 251 radially deeper and less numerous than produced from standard crimping techniques. Having sparsely crimped tubular legs 252 reduces the elongation properties of the bifurcated graft 250. Also, a sparsely crimped graft is easier to pack into the capsule jacket than a standard crimped graft. The low bulk and low elongation of the crimped graft further allows that the inferior ends of the graft may be packed into smaller diameter capsules. Similarly, the low crimp elongation factor allows for a higher degree of placement accuracy in conjunction with marker bands on the hypotube of the balloon catheter to adjust for the physiologic length of the crimped graft.

Whereas the standard crimp have peak widths of about two times the graft wall thickness, the crimps 251 of the bifurcated graft 250 may be of sufficient width, preferably two millimeters, so as to sew in radiopaque markers 255 on the face of selected crimps. The radiopaque markers are preferably "C" shaped and are secured to the edge of the crimp, allowing for twist detection under fluoroscopy. Similarly, long radiopaque markers 256 and short radiopaque markers 257 are secured to the edge of the main tubular member 253 to ensure proper alignment of the graft 250.

The distance between the crimps 251, or crimp pitch, is preferably less than the diameter of the tubular legs 252, so as to resist kinking. The crimp pitch is preferably 3.25 millimeters. The crimped graft 250 of the present invention is configured with crimps having peaks that are preferably one millimeter deep. So configured, the graft will maintain its high flexibility even under arterial pressures of over one hundred mm Hg within the corporeal lumen.

Referring to FIG. 18, a self-expanding superior attachment system 175 is secured adjacent the superior end 171 of the tubular member 170. As shown in FIG. 19, a first self-expanding inferior attachment system 176 is secured adjacent the inferior end of the ipsilateral tubular leg 171. Similarly, a second self-expanding inferior attachment system 176 is secured adjacent the inferior end of the contralateral tubular leg 172. Each attachment system serves to yieldably urge the graft 55 from a first compressed or collapsed position to a second expanded position and provides a fluid tight seal between the graft and corporeal lumen wall.

Each attachment system is formed of a plurality of vees 177 with the outer apices 178 and inner apices 179 of the vees being formed with helical torsion springs 180. The attachment system may be comprised of apices numbering from four to twenty-four. The springs yieldably urge the legs of each of the vees outwardly at a direction approximately at right angles to the plane in which each of the vees lie. The superior attachment system 175 has both long legs 181 and short legs 182 which stagger the apices along the superior end of the graft 55. The legs 183 of the inferior attachment system 176, however, are of equal length.

As shown in more detail in FIG. 20, the superior attachment system 175 is comprised of a single piece of wire which is formed to provide the vees 177 and also to define the helical torsion springs 180 between the legs 181 and 182. The two ends of the single piece of wire can be welded together in one of the legs to provide a continuous spring-like attachment system. In the construction shown in FIGS. 17 and 18, it can be seen that the attachment systems have twelve apices lying in three longitudinally spaced-apart parallel planes which are spaced with respect to the longitudinal axis of the main tubular member 170. The outer apices 178 residing external of the graft are staggered; whereas, the inner apices 179 residing within the graft lie in the same plane. Similarly, the apices will lie in four planes if the inner apices are also staggered.

The superior and inferior attachment systems 175 and 176 are secured to the wall 173 of the graft 55 by suitable means such as a polyester-suture material. As shown in FIGS. 18 and 19, sutures or knots 190 are used for sewing the inner apices 179 onto the wall of the main tubular member 170 and each tubular leg 171 and 172. Additional sutures 191 are preferably formed on each of the superior legs 181 and 182 to firmly secure each leg to the graft. The legs may be secured so that the apices lying in each plane are staggered to provide for the minimum profile when the attachment system is placed in its collapsed condition.

As shown in FIG. 20, wall engaging members 193 are preferably secured to the legs 181 and 182 of the attachment systems 175 and 176 in the vicinity of the outer apices 178 by suitable means such as a weld 194. The wall engaging members have a diameter ranging from 0.007 to 0.018 inches (0.254–0.457 mm) and a length from 0.5 to 5.0 millimeters. The wall engaging members are preferably sharpened to provide conical tips 195, and should have a length which is sufficient for the tip to penetrate into and perhaps through the corporeal lumen wall. The wall engaging members of the inferior attachment system 176 are configured in a similar manner.

The superior attachment system 175, inferior attachment system 176 and the wall engaging members 193 secured thereto are formed of a corrosion resistant material which has good spring and fatigue characteristics. One such material found to be particularly satisfactory is "ELGILOY" which is a cobalt-chromium-nickel alloy manufactured and sold by Elgiloy of Elgin, Ill. The wire can have a diameter ranging from 0.006 to 0.016 inches (0.203–0.406 mm), with a smaller diameter wire being utilized for the smaller diameter grafts. For example, 0.012 to 0.016 inch (0.305–0.406 mm) diameter wire for the frame and wall engaging members may be used in the larger grafts of eighteen to twenty-eight millimeters diameter, and 0.008 to 0.012 inch (0.203–0.305 mm) diameter wire may be used in the smaller grafts being eight to sixteen millimeters in diameter.

It has been found that the spring force created by the helical torsion springs 180 at the apices 178 and 179 is largely determined by the diameter of the wire. The greater the diameter of the wire, the greater the spring force applied to the legs 181 and 182 of the vees. Also, the longer the distances are between the apices, the smaller the spring force that is applied to the legs. It therefore has been desirable to provide a spacing of approximately fifteen millimeters between the outer extremities of the legs 181 of the superior attachment system 175. Similarly, a spacing of approximately ten millimeters between the outer extremities of the legs 183 of the inferior attachment system 176 is preferable, although smaller or larger distances may be utilized.

FIG. 21 shows a low stress configuration of an superior attachment system 175 or inferior attachment system 176. An additional helical torsion apex 185 is added along the legs 181, 182 or 183 of the attachment system. The additional apices are located adjacent the apices at the vees 177 formed by the legs. Such a configuration improves the fatigue characteristics of the attachment system. In addition, the weld 194 for the wall engaging members 193 may be moved down the attachment system leg 181 or 182 to improve fatigue life. Alternatively, a non-round or non-circular wire, for example, a rectangular, conical or rounded ribbon wire, may be used to reduce the amount of stress in the attachment system and still maintain the spring force of the attachment system.

To facilitate securing the graft 55 in the corporeal lumen, the conical tips 195 of the wall engaging members 193 on the superior attachment system 175 may be angled with respect to longitudinal axis of the main tubular member 170. The wall engaging members face outwardly from the main tubular member to facilitate holding the graft in place. Preferably, the conical tips of the wall engaging members on the superior attachment system are inclined from the longitudinal axis and toward the inferior end of the graft by 55° to 90° and preferably about 85°. Likewise, the conical tips 196 of the wall engaging members on the inferior attachment system 176 may be inclined towards the superior end of the graft by 30° to 90° and preferably 85°. By angling the conical tips of the wall engaging members so that they resist the force of the blood flow, the implanted wall engaging members oppose migration of the graft.

The helical torsion springs 180 placed at the apices 178 and 179 serve to facilitate compression of the graft 55 to place the superior and inferior attachment system 175 and 176 within the capsule assemblies 90, 130 and 200, as hereinafter described. The compression of the graft is accomplished by deformation of the helical torsion springs to just outside their elastic limit, thereby having a small component within the plastic range. Placing the apices in different planes and staggering or offsetting the wall engaging members 193 significantly reduces the minimum compressed size of the graft. Having the conical tips 195 and 196 in different planes also helps to prevent the wall engaging members from becoming entangled with each other. The natural spring forces of the helical torsion springs serves to expand the graft to its expanded position as soon as the attachment system is free of the capsules.

The graft 55 preferably contains a radiopaque marker system for locating the graft and for detecting any twisting of the graft during deployment. As shown in FIG. 17, the radiopaque marker system is comprised of two sets of relatively long radiopaque markers 197 and two sets of relatively short radiopaque markers 198. The radiopaque markers are made of a suitable material such as a platinum tungsten alloy wire of a suitable diameter such as 0.004 inches (0.102 mm) which is wound into a spring coil having a diameter of 0.4 inches (1.0 mm). The radiopaque markers are secured to the wall 173 by sutures, using the same material used to secure the attachment system to the graft.

As shown in FIG. 17, the long radiopaque markers 197 are located on the wall 173 of the graft 55 in a line parallel to the longitudinal axis of the main tubular member 170 and extend along the outside of the tubular legs 171 and 172. The first marker is positioned 0.5 centimeters from the superior attachment system 175. Additional markers are positioned intermittently thereafter for the length of the graft. The last marker in each set is 0.6 centimeters away from the inferior attachment system 176. Each long marker has a preferred length of three millimeters. Thus, the total number of markers in each set depends upon the length of the graft.

Each of the second set of radiopaque markers 198 preferably has a smaller length, for example two millimeters, and are positioned along the longitudinal axis of the inside of the tubular legs at a position 180° from the first set of markers 197. By placing markers of different lengths along the axis of the graft 55, it is possible to ascertain the position of the graft and to determine whether the ipsilateral and contralateral tubular legs have twisted between their superior and inferior ends. Under fluoroscopy, the two sets markers will be exhibited as two relatively straight lines for an untwisted graft, wherein a twisted graft will be revealed by a non-linear pattern of markers. By placing the markers at equal increments apart, it is possible to use fluoroscopy to ascertain longitudinal compression or tension on the graft.

As shown in FIGS. 37–39, the preferred radiopaque marking system for a bifurcated graft 250 having crimped tubular legs 252 includes one millimeter wide by five millimeter long marker coils 255 sewn to the tubular legs. The tubular leg marker coils are sewn horizontally every one centimeter on the same longitudinal axis as the long and short radiopaque markers 256 and 257 sewn on the main tubular member. The radiopaque marker configuration for the main tubular member remains the same as described above (FIG. 17). When detecting twist of the graft under fluoroscopy, the tubular leg markers appear with varying widths, ranging from one to five millimeters. The tubular leg markers, however, appear uniform in size for a tubular leg that is not twisted.

The sizing of the graft 55 may be performed on a patient-by-patient basis, or a series of sizes may be manufactured to adapt to most patient needs. For the repair of an aortic aneurysm, the length of the graft is selected so to span approximately one centimeter superior and one centimeter inferior of the aneurysm, wherein the wall engaging members 193 of the graft can seat within normal tissue of the vessel on both sides of the aneurysm. Thus, the graft should be about two centimeters longer than the aneurysm being repaired. During the preimplant fluoroscopy procedure, a conventional pigtail angiography catheter is used to determine the locations of the renal arteries to ensure the renal arteries will not be covered by the implanted graft. Likewise, on the inferior end of the corporeal lumen, determining the location of the internal iliac arteries ensures that they will not be covered by the implanted graft. Also, the diameter of the main tubular member 170 is selected by measuring the corporeal lumen which will receive the graft by conventional radiographic techniques and then selecting a graft with a main tubular member having a diameter at least one millimeter larger than that measured.

FIGS. 22 and 23 show an alternative embodiment of the intraluminal graft 55. A segment of polyester yarn 199 or similar material is used to produce a "fuzzy" thrombogenic surface to reduce blood leakage and improve blood clotting and coagulation along the superior end of the main tubular member 170. The filaments of the yarn segment are teased apart to increase the embolization area. The yarn segment is sutured to the wall 173 of the graft between one or more of the vees 177 of the superior attachment system 175.

FIG. 22 shows the yarn segment 199 positioned on the graft wall 173 inside an outer apex 178; however, the yarn segment may also be positioned within the vee of an inner apex 179. Similarly, yarn segments may be attached to the graft wall adjacent the inferior attachment systems 176 on the ipsilateral and contralateral tubular legs 171 and 172. Alternatively, the graft may be made of velour or terry to similarly occlude blood flow through the ends of the graft adjacent the attachment system. Likewise, other modifications to the graft wall may be made to accomplish the same result.

FIGS. 1, 7, 8, 24 and 27 show the contralateral capsule assembly 200 comprising a contralateral capsule 202 and a guiding tube assembly 205. The purpose of the contralateral capsule is to retain the inferior attachment system 176 secured to the contralateral tubular leg 172. The guiding tube assembly is used to pull the contralateral capsule into the contralateral artery, e.g., iliac, and is configured to deploy the inferior attachment system when the contralateral tubular leg is properly positioned. The contralateral capsule is also configured to connect with a torque catheter 215 to aid in proper deployment of the contralateral tubular leg.

As shown in FIG. 27, the contralateral capsule 202 is of sufficient length to contain the contralateral inferior attachment system 176 secured to the contralateral tubular leg 172. The contralateral capsule prevents the conical tips 196 of the wall engaging members 193 from contacting the wall of the body lumen prior to deployment of the attachment system. The contralateral capsule is made from stainless steel or similar biocompatible material. The contralateral capsule is typically 1.5 centimeters long with a internal diameter of 0.3 centimeters. The contralateral capsule is preferably circular shaped so as to fit within the indentation of the proximal capsule 132, as shown in FIG. 28, and is open at its distal end to receive the inferior attachment system. In addition, the contralateral capsule may be configured with an indentation (not shown) to prevent the inferior attachment system from rotating within the contralateral capsule.

A barbed adapter 203 is fitted within the proximal end of the contralateral capsule 202 to couple to the distal end of the torque catheter 215. The barbed adapter is formed around a polyethylene guiding tube 206 which comprises the distal length of the guiding tube assembly 205. The distal end of the guiding tube is flared and expanded just distal of the barbed adapter. A retaining bump 204 may be formed on the guiding tube just proximal of the barbed adapter to secure the adapter in place. As shown in FIG. 8, the barbed adapter is further configured with a bore in which the guiding tube resides.

A distal locking ball 208 and a proximal locking ball 209 are fixed at the distal end of a pull wire 207 about 1.2 centimeters apart and reside within the contralateral capsule. Prior to deployment of the contralateral tubular leg 172 into the contralateral iliac artery, the inferior attachment system 176 resides in the contralateral capsule between the distal and proximal locking balls. As shown in FIG. 27, the contralateral capsule assembly may be configured with only the distal locking ball, when the inferior attachment system does not need to be pushed from the contralateral capsule.

The guiding tube assembly 205 comprises the pull wire 207 disposed within the distal guiding tube 206 and a proximal guiding tube 213. Approximately a distance equal to the length of the graft 55 from the contralateral capsule 202, or distal end of the guiding tube, a six centimeter segment of the guiding tube is configured with a radiopaque material, such as a platinum coil 210. As shown in FIGS. 1 and 8, the radiopaque material marks the point where the guiding tube exits the distal end 163 of the capsule jacket 160. Such a marking allows fluoroscopic determination of whether the guiding tube has been twisted or wrapped around the capsule jacket or distal capsule assembly 90.

The guiding tube assembly 205 is further configured with a tapered joint 211 approximately fifty centimeters from the contralateral capsule 202. The tapered joint connects the distal guiding tube 206 with a proximal guiding tube 213. The tapered proximal end of the distal guiding tube nests inside the flared distal end of the proximal guiding tube. Both guiding tubes are preferably made from polyethylene tubing or similar material. The proximal end of the proximal guiding tube is connected to a 0.035 inch (0.9 mm) diameter contralateral "J" guide wire 212 made from stainless steel and having a length of about seventy centimeters.

The pull wire 207 extends from the contralateral capsule 202 to a point just distal the proximal end of the proximal guiding tube 213. The pull wire is fixed at its proximal end to the proximal guiding tube to prevent relative movement between the parts of the guiding tube assembly 205 such that pulling on the contralateral guide wire 212 or the proximal guiding tube will cause corresponding movement of the contralateral capsule. If, however, the guiding tube assembly 205 is cut somewhere between the tapered joint 211 and the contralateral guide wire, then the proximal portion of the proximal guiding tube can be removed from the pull wire. Once the assembly is cut, the contralateral capsule can be moved relative to the pull wire by sliding the distal guiding tube 206 proximally over the pull wire. Black or colored marker bands 214 formed from PET shrink tubing are positioned at predetermined locations on the proximal guiding tube to indicate the chronological order in which the sections of the guiding tube assembly is removed during the deployment process.

A torque catheter assembly 215 for use with the contralateral capsule assembly 200 is shown in FIG. 24. The torque catheter assembly consists of a torque catheter shaft 216 made of a flexible plastic material, such as PEBAX. The shaft is of sufficient length to span the distance from the contralateral femoral cutdown to the position in the contralateral iliac artery where the contralateral attachment system 176 is to be deployed, for example, forty centimeters. The torque catheter shaft is provided with a through lumen configured to accept and pass over the proximal and distal sections 213 and 206 of the guiding tube assembly 205.

The distal end 217 of the torque catheter shaft 216 is configured to connect to the barb adapter 203 on the contralateral capsule 202. The distal end of the shaft is further configured with a radiopaque marker band 218 for use in securing the distal end of the torque catheter to the barb adapter. Alternatively, the distal end of the shaft may be configured with a radiopaque adapter configured to mate with the barb adapter. The distal end of the torque catheter shaft is preferably provided with one or more purge ports 219.

The proximal end 221 of the torque catheter assembly 215 is provided with a stop cock 222 having a female Luer fitting 223 for injecting a fluid for purging the torque catheter shaft lumen 220. Likewise, a contrast fluid may be injected through the Luer fitting and out the distal end 217 or purge ports 219 of the torque catheter shaft. The proximal end of the torque catheter shaft is further provided with two consecutive Touhy Borst adapters 240 and 241 separated by a single lumen polyethylene tube 242.

The distal Touhy Borst adapter 240 locks on the distal guiding tube 206 with the barb adapter 203 engaging the distal end 217 of the torque catheter shaft 216. This engagement allows torque ability of the contralateral capsule 202. The proximal Touhy Borst adapter 241 engages the proximal guiding tube 213 and ultimately the pull wire 207 which secures the contralateral attachment system 176 within the contralateral capsule. The tapered joint 211 between the distal guiding tube and the proximal guiding tube resides between the two Touhy Borst adapters.

The distal end of the single lumen polyethylene tube 242 is flared and secured to the cap of the distal Touhy Borst adapter 240. The proximal end of the polyethylene tube is configured with a barbed female Luer fitting 243 on which the proximal Touhy Borst adapter 241 is secured for engaging the proximal guiding tube 213. To expose the pull wire 207, the proximal Touhy Borst is unlocked and removed from the female Luer, thereby removing the proximal guiding tube 213 with the proximal Touhy Borst adapter.

FIG. 8 depicts the distal end of the intraluminal grafting system 50 assembled for deployment. The distal cap 92 is in its retracted or proximal position adjacent to proximal cap 100. Similarly, core wire 91 is locked via control knob 113 in its retracted or proximal position. During initial deployment, capsule catheter tubular member 131 is in its most distal position in relation to balloon catheter assembly 51 and is locked in place by the locking ring on the Touhy Borst adapter 147.

The graft 55 is disposed within the distal capsule 93, the proximal capsule 132, the contralateral capsule 202 and the capsule jacket main sheath 160. The superior end of the main tubular member 170 and superior attachment system 175 are removably retained within the distal capsule 93. The inferior end of the ipsilateral tubular leg 171 and inferior attachment system 176 are removably retained within the proximal capsule 132. Likewise, the inferior end of the contralateral tubular leg 172 and inferior attachment system 176 are removably retained within the contralateral capsule 202.

During initial deployment, the distal end of the balloon catheter 80 is positioned such that the distal stem 82 of the balloon 60 resides within the main tubular member 170 of the graft 55, as shown in FIG. 8. The proximal cap 100 is positioned just proximal the distal cap 92 and is disposed within the distal capsule 93. In addition, proximal locking ring 86 and distal locking ring 87 are disposed on either side of the ipsilateral attachment system 176. Similarly, proximal locking ball 209 and distal locking ball 208 are disposed on either side of the contralateral attachment system 176. In the preferred embodiment, distal locking ring 87 and distal locking ball 208 are disposed just distal of the respective attachment systems 176. Also, the capsule jacket assembly 53 is positioned such that the distal end 163 of the capsule jacket main sheath 160 overlaps at least a portion of the distal capsule. During deployment, capsule jacket locking connector 162 secures the main sheath in place. Thus, when any movement or force is applied to the handle assembly 110, the entire apparatus 50 moves as a single unit.

By way of example, the following describes a method of repair of an aortic aneurysm using the method comprising the present invention for intraluminal placement of a graft in an aorta. First, a patient is prepared in a conventional manner by use of a guide wire 56, a dilator and sheath (not shown) to open both ipsilateral and contralateral femoral arteries or vessels of the patient. The contralateral guide wire 212 is then used to feed the guiding tube assembly 205 through the cutdown in the ipsilateral femoral artery and ipsilateral iliac artery 228 into the aorta. By conventional means, a basket catheter or similar device is fed through a cutdown in the contralateral femoral artery to the contralateral iliac artery 229 to snare or capture the proximal end of the guiding tube assembly. The guiding tube 206 is then pulled through the contralateral iliac artery and out the cutdown in the contralateral femoral artery.

The distal end of the intraluminal grafting apparatus 50 is then inserted into the sheath, which has previously been placed in the femoral artery. In the preferred embodiment of the present invention, balloon catheter lumen 63 is provided for receiving the guide wire 56 that was previously traversed across the aneurysm. However, the following procedure may also be used when the guiding member is constructed as part of the balloon catheter.

Next, the balloon catheter assembly 51, the capsule catheter assembly 52, the capsule jacket assembly 53 and the control wire assembly 54 are all configured for deployment as shown in FIGS. 1 and 8. Thus, the assemblies may be advanced by the physician as a single unit over the main guide wire 56. As shown in FIG. 29, the main guide wire is introduced by the physician into a cutdown in the ipsilateral femoral artery and advanced through the ipsilateral iliac artery 228 to the desired location in the abdominal aorta 225 and adjacent to the diseased or damaged portion 226 of the vessel.

The physician advances the distal end of the intraluminal grafting assembly 50 through the ipsilateral femoral artery over the guide wire 56 while maintaining slight tension on the guiding tube assembly 205 from the cutdown in the contralateral femoral artery. Typically, the desired position for implanting the graft 55 will be within the abdominal aorta 225 with the superior extremity of the main tubular member 170 at least one centimeter inferior to the lower renal artery. The inferior attachment systems 176 should be positioned 0.5 centimeters superior the internal iliac arteries. However, prior to removing the contralateral tubular leg 172 from the capsule jacket assembly 53, the proximal capsule assembly 130 and contralateral capsule assembly 200 must be positioned superior the bifurcation of the abdominal aorta to the ipsilateral iliac artery 228 and contralateral iliac artery 229, as shown in FIG. 29. Fluoroscopy is used to inspect the position of the radiopaque section 210 of the guiding tube assembly 205 to ensure that the distal end of the guiding tube 206 is not wrapped or twisted around the distal capsule assembly 90 as the distal capsule 93 first enters the aorta.

Figure 30:
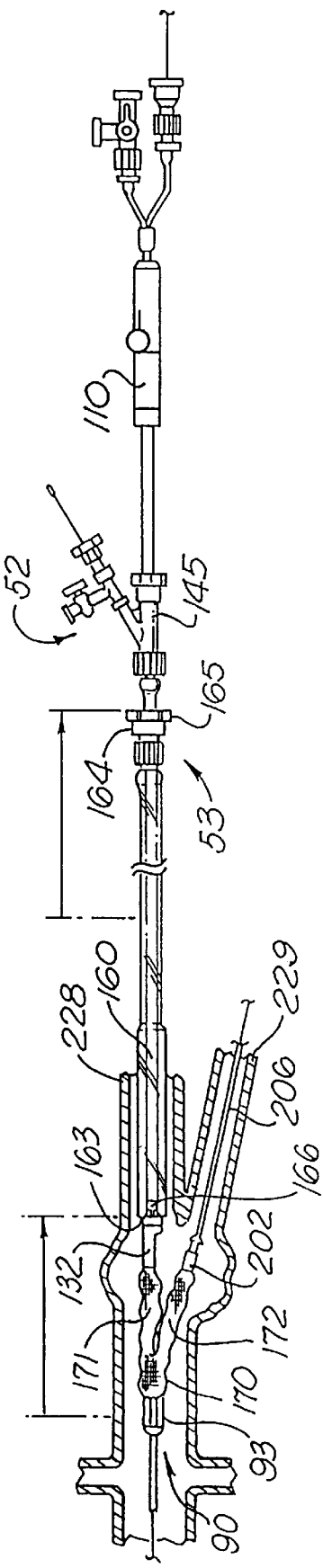
FIG. 30 is a partial cross-sectional view of the intraluminal grafting system, wherein the capsule jacket has been withdrawn from the graft.

When the proximal capsule assembly 130 and the contralateral capsule assembly 200 are in the desired position, as shown in FIG. 29, the locking ring 165 of the capsule jacket assembly 53 is loosened to allow movement of the capsule jacket main sheath 160. While using one hand to firmly grasp the capsule catheter assembly 52 and hold it stationary, the physician grasps the sheath adapter 164 with the other hand and gently pulls the sheath adapter proximally towards the capsule catheter wye adapter 145. Simultaneously, the physician applies slight tension on the guiding tube assembly 205 from the contralateral side as it is removed from the capsule jacket assembly. The capsule jacket assembly is gradually retracted to sufficiently expose the proximal capsule 132 to free the contralateral capsule 202. The locking ring is then tightened to hold the capsule jacket assembly in place such that the distal end 163 of the capsule jacket rests near the proximal end of the proximal capsule, as shown in FIG. 30. The radiopaque marker 166 at the distal end of the capsule jacket main sheath may be used to position the capsule jacket relative to the proximal capsule. In the alternative embodiment where the crimped graft 250 is used, the position of the distal capsule 93 relative to the proximal capsule 132 is adjusted by using the marker bands on the hypotube 115 to adjust the implant length to physiologic length.

Figure 31:
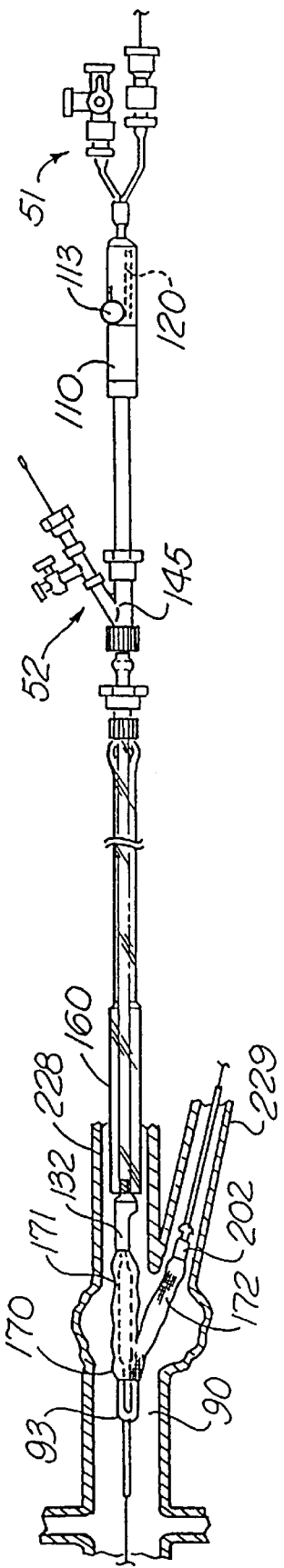
FIG. 31 is a partial cross-sectional view of the intraluminal grafting system, wherein the contralateral tubular leg and contralateral capsule assembly have been pulled into the contralateral iliac artery.

At this point in the procedure, the contralateral tubular leg 172 of the graft 55 is moved into the contralateral iliac artery 229 by pulling the guiding tube 206 in a proximal direction, as shown in FIG. 31. At the same time and with concurrent motion, the superior end of the main tubular member 170, disposed in the distal capsule 93, is moved into the desired location of the aorta 225 by moving the control handle 110, and thereby the intraluminal grafting assembly 50, in a proximal direction. By this motion, the inferior end of the ipsilateral tubular leg 171, securely retained within the proximal capsule 132, is moved to the desired location in the ipsilateral iliac artery 228 for deploying the ipsilateral attachment system 176. Similarly, the inferior end of the contralateral tubular leg, securely retained with in the contralateral capsule 202, is positioned for deployment of the contralateral attachment system. Thus, each of the attachment systems should be in position for deployment.

The control knob 113 is then rotated to cause relative movement between the distal capsule assembly 90 and the balloon catheter assembly 51 to release the superior end of the main tubular member 170 and superior attachment system 175 from the distal capsule 93. Rotating the control knob causes the retaining rack 120 to move the control wire 91 in a distal direction. Since the distal cap 92 and distal capsule 93 are secured to the control wire 91, they move in corresponding relationship with the rotation of the control knob. As the distal capsule is moved from engagement with the superior attachment system, the balloon catheter proximal cap 100 locates at the proximal end of the distal capsule. As soon as the distal capsule has cleared the superior attachment system 175, the superior extremity of the main tubular member expands outwardly under the force of the self-expanding attachment system which springs into engagement with the vessel wall 202. The locking pin 126 holds the control knob, and thus the control wire and distal capsule, fixed in place.

Once the superior attachment system 175 is exposed, steps are taken to firmly seat or urge the wall engaging members 193 in the vessel wall. First, the locking ring on the capsule catheter Touhy Borst adapter 147 is loosened to permit relative movement between the capsule catheter assembly 52 and the balloon catheter assembly 51. While the physician uses one hand to hold the capsule catheter assembly stationary, the handle assembly 110 is grasped by the other hand and pushed distally to position the center of the main balloon 60 into the superior extremity of the main tubular member 170. The radiopaque marker 84 is used to align the main balloon and superior attachment system.

Figure 32:
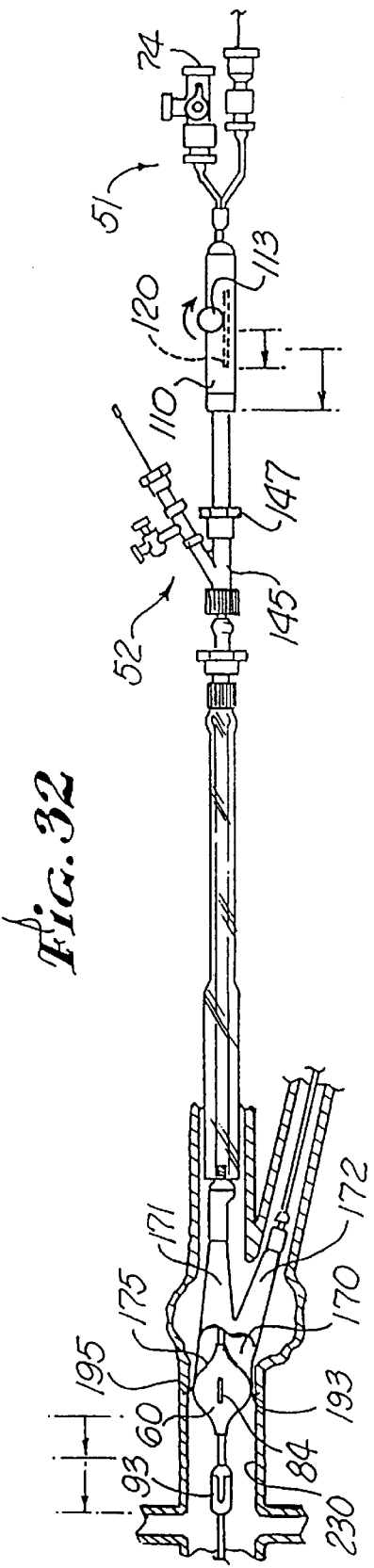
FIG. 32 is a partial cross-section view of the intraluminal grafting system, wherein the distal capsule has been removed from the superior end of the main tubular member and the inflatable member has been expanded to seat the superior attachment system.

Thereafter, a conventional hand operated syringe or inflation assembly (not shown) is attached to the balloon catheter inflation port 74. As depicted in FIG. 32, the main balloon 60 is then expanded by introducing a suitable gas such as carbon dioxide or a dilute radiopaque liquid from the syringe to urge the wall engaging members 193 outwardly to firmly emplace the superior conical tips 195 into the vessel wall 230. The main balloon may be deflated and inflated repeatedly to ensure the superior attachment system is firmly implanted in the vessel.

The main balloon 60 normally remains in an inflated position during the next steps of the procedure. During the actual retraction of the contralateral capsule 202 and proximal capsule 132, the main balloon should be inflated, further securing the superior attachment system 175. However, the main balloon may be deflated and reinflated during the following steps to allow the tubular legs 171 and 172 to fill with blood to facilitate detecting any twisting of the bifurcated graft 55.

As shown in FIG. 33, the next step is to implant or anchor the inferior attachment system 176 of the contralateral tubular leg 172. Initially, the proximal guiding tube 213 is cut between the single and double marker bands 214. Next, the portion of the guiding tube containing the single marker band is removed. Then, the torque catheter assembly 215 is passed over the remaining guiding tube assembly 205 so as to engage the distal connector 217 of the torque catheter with the barb adapter 203 of the contralateral capsule assembly 200, as depicted in FIG. 24. The torque catheter is used to straighten any twists in the guiding tube and can be used to adjust the placement of the contralateral capsule 202. The torque catheter may remain secured to the contralateral capsule assembly during the following procedure with the two Touhy Borst adapters 240 and 241 locked to the distal and proximal guiding tubes 206 and 213.

Next, the proximal guiding tube 213 is cut proximal of the tapered joint 211 between the double and triple marker bands 214 to allow relative movement between the distal section of the guiding tube 206 and the pull wire 207. Then, the portion of the guiding tube containing the double marker band is removed. The proximal Touhy Borst adapter 241 of the torque catheter assembly 215, which is locked to the proximal guiding tube, is disengaged from the Luer fitting 243 exposing the pull wire 207. Thus, the proximal guiding tube having the triple marker band is also removed. The pull wire and locking ball 208 are then advanced into the contralateral tubular leg 172 by moving the pull wire distally.

The torque catheter assembly 215 and distal guiding tube 206 are then moved in a proximal direction to remove the contralateral capsule 202 from the inferior attachment system 176 while the pull wire 207 is held fixed relative to the torque catheter assembly. The distal end of the pull wire and locking ball 208 remain in place inside the contralateral tubular leg 172. Once the inferior extremity of the contralateral tubular leg is free of the contralateral capsule, the inferior attachment system will spring open and the wall engaging members 193 will engage the contralateral iliac artery wall 231.

Thereafter, the torque catheter 215 and/or guiding tube 206 and contralateral capsule 202 are removed through the contralateral femoral artery cutdown. The pull wire 207 is moved distally so that the locking ball 208 is disposed near the superior end of the contralateral tubular leg 172. A conventional (contralateral) balloon catheter 235 is then moved into the contralateral iliac artery 229 over the pull wire and positioned within the inferior attachment system 176. A contralateral balloon 236 configured on the contralateral balloon catheter is then inflated to firmly seat the conical tips 196 of the inferior attachment system into the contralateral iliac artery wall 231. The contralateral balloon may be deflated and reinflated throughout the contralateral tubular leg to open the entire length of the tubular leg. The contralateral balloon catheter remains in place with the contralateral balloon inflated during the next sequence of steps; however, the contralateral balloon catheter, pull wire and locking ball may be removed once the contralateral attachment system is firmly implanted.

As shown in FIG. 34, the next step is to deploy the inferior attachment system 176 of the ipsilateral tubular leg 171 into the ipsilateral iliac artery 228. First, the ipsilateral lock adapter 153 is loosened to release the ipsilateral locking wire 85. The ipsilateral locking wire proximal handle 88 is then moved distally to advance the locking rings 87 into the superior portion of the ipsilateral tubular leg. Next, the locking mechanism 147 of the capsule catheter wye adapter is loosened. With the handle assembly 110 of the balloon catheter assembly 51 held firmly in place, the capsule catheter assembly 52 is moved proximally until the inferior attachment system and inferior end of the ipsilateral tubular leg are completely clear of the proximal capsule 132.

Once the inferior extremity of the ipsilateral tubular leg 171 is free of the proximal capsule 132, the ipsilateral inferior attachment system 176 will spring open and the wall engaging members 193 will engage the ipsilateral iliac vessel wall 232. Leaving the main balloon 60 inflated while the capsule catheter assembly 52 is moved ensures that the superior attachment system 175 will remain firmly secured in place. Thereafter, the ipsilateral locking wire 85 is moved proximally to its original position and is secured by tightening the locking wire adapter 153.

Figure 35:
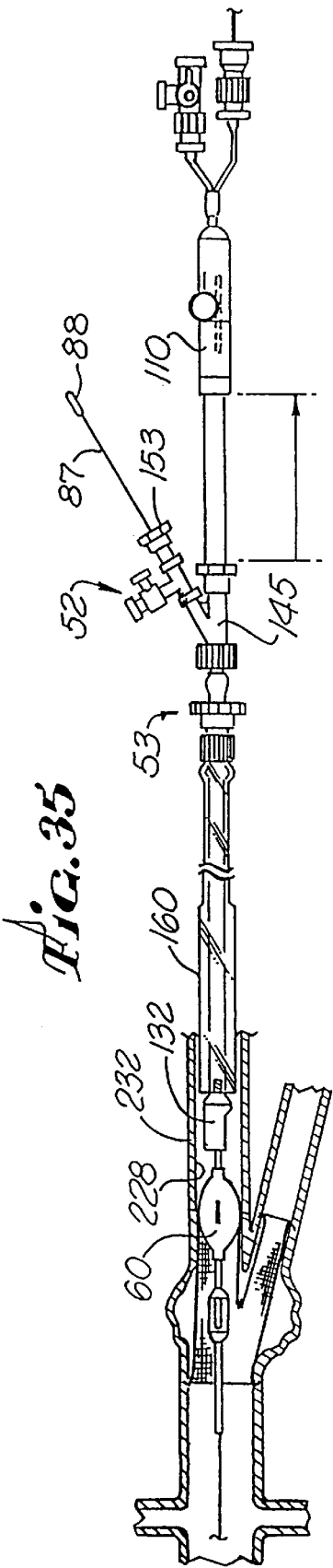
FIG. 35 is a partial cross-sectional view of the intraluminal grafting system, wherein the inflatable member of the balloon catheter has been moved and inflated proximate the inferior attachment system of the ipsilateral tubular leg.

Next, the main balloon 60 is deflated. As shown in FIG. 35, the handle assembly 110 is moved proximally so that the main balloon is retracted into the ipsilateral tubular leg 171 and placed adjacent the ipsilateral inferior attachment system 176. If the main balloon cannot be positioned adjacent to the ipsilateral attachment system due to limited available movement of the handle assembly, then the capsule catheter locking ring 147 is secured to the hypotube 115, thereby securing the capsule catheter assembly to the balloon catheter assembly 51. The entire deployment catheter 50 is then moved proximally to position the main balloon adjacent the ipsilateral attachment system.

The main balloon 60 may be inflated and deflated through the entire length of the main tubular member 170 and ipsilateral tubular leg 171 to ensure patency of the bifurcated graft 55. Again, the balloon radiopaque marker 84 is used to align the center of the main balloon with the ipsilateral attachment system 176. The balloon is then inflated just enough to expand the ipsilateral attachment system to tack down the wall engaging members 193 into the ipsilateral iliac artery vessel wall 232. Thereafter, the main balloon is finally deflated.

Figure 36:
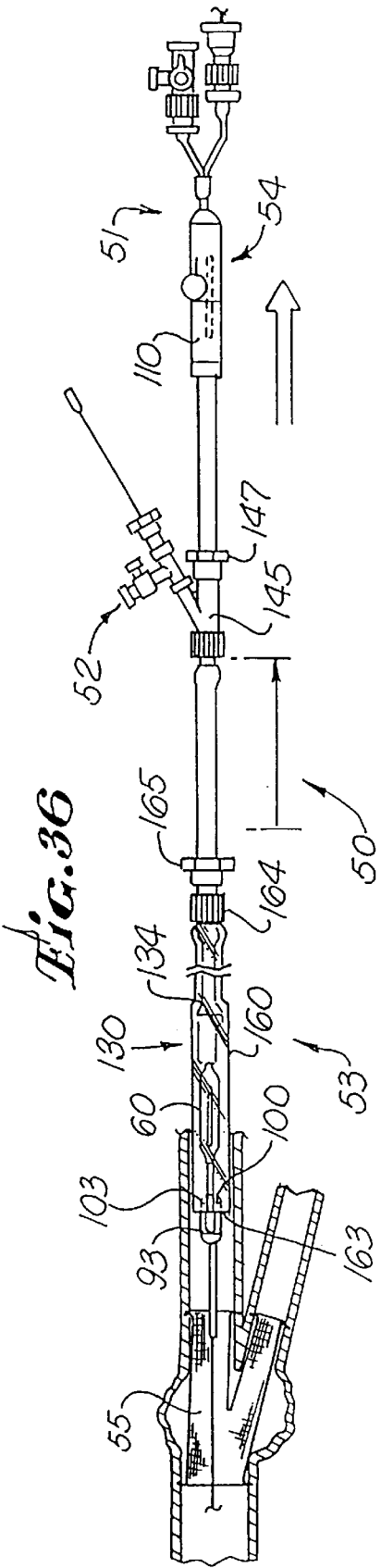
FIG. 36 is a partial cross-sectional view of the intraluminal grafting system, wherein the balloon catheter, capsule catheter and capsule jacket have been placed in a position for withdrawal from the corporeal lumen.

As shown in FIG. 36, the proximal capsule assembly 130 and balloon 60 are moved proximal the graft 55. First the locking ring 147 is loosened. Then, while holding the capsule catheter assembly 52 in place by grasping the wye adapter 145 with one hand, the balloon catheter assembly 51 is moved proximally by gently pulling the handle assembly 110 with the other hand. Thus,. the capsule catheter assembly and balloon catheter are in the same relative position as they were just prior to deployment (FIG. 8). Also, the proximal end 103 of the distal capsule 93 has been mated with the proximal cap 100 for smooth transition.

Finally, the capsule jacket locking ring 165 is loosened. While holding the capsule jacket sheath adapter 164 in place, the balloon catheter assembly 51 and capsule catheter assembly 52 are moved proximally and in unison by gently pulling the wye 145 of the capsule catheter assembly. The catheter assemblies are moved until the distal end 163 of the capsule jacket main sheath 160 covers the proximal cap 100 or until the proximal capsule adapter housing 134 mates with the flared transition of the capsule jacket, thereby creating a smooth transition along the entire length of the intraluminal grafting apparatus 50. Thereafter, the balloon catheter assembly, capsule catheter assembly, capsule jacket assembly 53 and control wire assembly 54 are removed from the aorta through the femoral artery. The graft 55 and attachment systems 175 and 176 remain secured to the vessel walls 230, 231 and 232, thereby sealing the aneurysm 226 from blood flow.

When the intraluminal grafting apparatus 50 is removed from the ipsilateral iliac and femoral arteries, the main guide wire 56 remains in place in the vessels. A conventional (ipsilateral) auxiliary balloon catheter (not shown) is traversed over the main guide wire and positioned at the inferior end of the ipsilateral tubular leg 171 and within the ipsilateral attachment system 176. An ipsilateral auxiliary balloon on the ipsilateral auxiliary balloon catheter is inflated to firmly implant the conical tips 196 of the wall engaging members 193 into the ipsilateral iliac artery wall 232. The ipsilateral auxiliary balloon may be inflated and deflated along the entire ipsilateral tubular leg to ensure the tubular leg is completely open and to remove creases which may have set while the graft was loaded in the capsule jacket assembly. Thereafter, the ipsilateral auxiliary balloon catheter and main guide wire are removed from the ipsilateral femoral artery and the cutdowns are closed.

The entire procedure described herein can be observed under fluoroscopy. The relative positioning of the graft 55 and the balloon 60 can be readily ascertained by the radiopaque attachment systems 175 and 176, radiopaque locking mechanisms 87 and 208, radiopaque markers 197 and 198 provided on the graft, the radiopaque marker 84 on the balloon shaft 61 and the proximal cap 100. If any twisting of the graft has occurred between placement of the superior attachment system and the inferior attachment system, then the twisting can be readily ascertained by observing the series of markers 197 and 198. Adjustments to eliminate any twisting which may have occurred can be made before exposing the attachment systems by rotation of the balloon catheter 51, the capsule catheter assembly 52 or the contralateral capsule 132 via the torque catheter 215. Any excessive graft compression can be ascertained by observing the radiopaque markers under fluoroscopy. Adjustments to eliminate graft compression can be made before exposing the inferior extremity of the graft by applying tension on the capsule catheter assembly and torque catheter 215.

As shown in FIGS. 40 and 41, if crimping of the tubular legs of the graft is not employed, then additional attachment systems 275 may be placed within the tubular legs to prevent kinking of the graft material in the tubular legs. As shown in FIGS. 40 and 41 these additional attachment systems 275 are placed medial the ends of the ipsilateral and/or contralateral tubular legs. Such medial attachment systems 275 resemble the inferior attachment systems 176 used to secure the ipsilateral 171 and contralateral 172 tubular legs, but the medial attachment system are preferably configured without wall engaging members. The medial attachment systems are deployed using an auxiliary capsule catheter traversed over the main guide wire 56 and the contralateral pull wire 207 or another guide wire inserted in the contralateral tubular leg 172 after the contralateral attachment system 176 is firmly seated.

Post implant fluoroscopy procedures can be utilized to confirm the proper implantation of the device by the use of a conventional pigtail catheter or by injecting dye into the guide wire lumen of the balloon catheter shaft. Thereafter the sheath can be removed from the femoral artery and the femoral artery closed with conventional suturing techniques. Tissues should begin to grow into the graft within two to four weeks with tissue completely covering the interior side of the graft within six months so that no portion of the graft thereafter would be in communication with the blood circulating in the vessel. This establishes a complete repair of the aneurysm which had occurred.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. A method for securing a bifurcated graft in a corporeal lumen, the bifurcated graft having a superior end, an ipsilateral inferior end and a contralateral inferior end, the bifurcated graft further having an anchoring system associated with each of the superior end, the ipsilateral inferior end and the contralateral inferior end, said method comprising the steps of:

providing a delivery catheter assembly having a distal covering assembly that receives the superior end of the bifurcated graft, an ipsilateral covering assembly that receives the ipsilateral inferior end and a contralateral covering assembly that receives the contralateral inferior end;

positioning the delivery catheter assembly and the bifurcated graft at a desired location within a corporeal lumen;

withdrawing the distal covering assembly from the superior end of the graft;

withdrawing the contralateral covering assembly from the contralateral inferior end of the bifurcated graft;

withdrawing the ipsilateral covering assembly from the ipsilateral inferior end of the bifurcated graft; and removing the delivery catheter from the corporeal lumen, wherein the bifurcated graft remains secured within the corporeal lumen.

2. The method of claim 1, wherein the positioning step includes placing the bifurcated graft proximate an aneurism proximate an aortic bifurcation.

3. A method for emplacement of a bifurcated graft in a corporeal lumen having a wall, the bifurcated graft having a plurality of attachment systems and being disposed within a delivery catheter assembly including a balloon catheter having a distal capsule, an inflatable member and a first shaft coupled to the distal capsule and the inflatable member, the delivery catheter assembly further including a capsule catheter having an ipsilateral capsule and second shaft coupled to the ipsilateral capsule, the delivery catheter further including a contralateral capsule assembly having a contralateral capsule, said method comprising the steps of:

manipulating the delivery catheter assembly to advance the bifurcated graft, the balloon catheter, the capsule catheter and the contralateral capsule into a corporeal lumen, wherein the bifurcated graft and each attachment system are removably retained in the distal, ipsilateral and contralateral capsules to prevent the attachment systems from contacting the corporeal lumen wall while the bifurcated graft is being advanced through the corporeal lumen;

positioning the bifurcated graft at a desired location in the corporeal lumen;

removing the attachment systems from the distal, ipsilateral and contralateral capsules;

inflating the inflatable member to engage at least one attachment system of the bifurcated graft so that the attachment system and the bifurcated graft are secured to the corporeal lumen wall;

deflating the inflatable member; and withdrawing the delivery catheter assembly from the bifurcated graft and from the corporeal lumen, wherein the bifurcated graft is retained within the corporeal lumen.

4. The method of claim 3, wherein the delivery catheter assembly further includes a capsule jacket coaxially disposed over the capsule catheter, and the balloon catheter is coaxially disposed within the capsule catheter, such that the capsule jacket covers the bifurcated graft, the ipsilateral capsule, the contralateral capsule and at least a portion of the distal capsule, said method further comprising the step of withdrawing the capsule jacket from the bifurcated graft prior to removing the attachment systems from the distal, ipsilateral and contralateral capsules.

5. A method for implanting a bifurcated graft in a corporeal lumen having a wall afflicted by an aneurysm having a superior end, the bifurcated graft including a superior attachment system having wall engaging members, an ipsilateral attachment system having wall engaging members and a contralateral attachment system having wall engaging members, said method comprising the steps of:

covering the ipsilateral attachment system of the bifurcated graft with an ipsilateral capsule, the ipsilateral capsule being coupled to a first shaft;

covering the superior attachment system of the bifurcated graft with a distal capsule, the distal capsule being coupled to a second shaft in fluid communication with a main balloon, wherein the second shaft is coaxially and slidably disposed within the first shaft;

covering the contralateral attachment system of the bifurcated graft with a contralateral capsule, the contralateral capsule being coupled to a pull wire;

covering the bifurcated graft, the ipsilateral capsule, the contralateral capsule and at least a portion of the distal capsule-and pull wire with a sheath slidably disposed over the first and second shafts;

introducing the bifurcated graft, distal capsule, ipsilateral capsule, contralateral capsule, pull wire, balloon and at least a portion of the first shaft, second shaft and sheath into a corporeal lumen;

positioning the bifurcated graft such that the superior attachment system is located superior to the superior end of the aneurysm;

removing the sheath from the distal capsule, the contralateral capsule and at least a portion of the ipsilateral capsule;

removing the distal capsule from the superior attachment system;

positioning the main balloon adjacent the superior attachment system;

inflating the main balloon to urge the wall engaging members of the superior attachment system into the wall of the lumen;

removing the contralateral capsule from the inferior attachment system and from the corporeal lumen;

inserting an auxiliary balloon into the corporeal lumen adjacent the contralateral attachment system;

inflating the auxiliary balloon to urge the wall engaging members of the contralateral attachment system into the wall of the lumen;

removing the ipsilateral capsule from the ipsilateral attachment system;

deflating the auxiliary balloon;

removing the auxiliary balloon from the corporeal lumen;

deflating the main balloon; positioning the main balloon adjacent the ipsilateral attachment system;

inflating the main balloon to urge the wall engaging members of the ipsilateral attachment system into the wall of the lumen;

deflating the main balloon; and removing the main balloon, distal capsule, ipsilateral capsule, first shaft, second shaft and sheath from the corporeal lumen, wherein the bifurcated graft is retained in the lumen.

6. The method of claim 5, wherein said introducing the bifurcated graft step includes providing-an opening in at least one femoral artery and said positioning the bifurcated graft step includes placing the bifurcated graft proximate an aortic bifurcation.

7. A method for engrafting a bifurcated prosthesis into a corporeal lumen, the bifurcated prosthesis having a superior end, an ipsilateral end and a contralateral end, the bifurcated prosthesis further having an anchoring device associated with each of the superior end, the ipsilateral end and the contralateral end, said method comprising the steps of:

(a) providing a delivery assembly, the delivery assembly comprises a distal covering device, an ipsilateral covering device and a contralateral covering device;

(b) providing a capsule jacket that removably receives the bifurcated prosthesis, the distal covering device, the ipsilateral covering device and the contralateral covering device;

(c) placing the superior end of the bifurcated prosthesis into the distal covering device;

(d) placing the ipsilateral end of the bifurcated prosthesis into the ipsilateral covering device;

(e) placing the contralateral end of the bifurcated prosthesis into the contralateral covering device;

(f) placing the bifurcated prosthesis and the delivery assembly into the capsule jacket;

(g) creating an opening in the corporeal lumen for transversing the capsule jacket, the delivery assembly and the bifurcated prosthesis therethrough;

(h) inserting the capsule jacket, the delivery assembly and the bifurcated prosthesis into the opening in the corporeal lumen;

(i) urging the bifurcated prosthesis to a desired location within the corporeal lumen;

(j) positioning the distal covering device at a desired location within the corporeal lumen;

(k) activating the anchoring system to secure the superior end of the bifurcated prosthesis within the corporeal lumen;

(l) positioning the contralateral covering device at a desired location within the corporeal lumen;

(m) activating the anchoring system to secure the contralateral end of the bifurcated prosthesis within the corporeal lumen;

(n) positioning the ipsilateral covering device at a desired location within the corporeal lumen;

(o) activating the anchoring system to secure the ipsilateral end of the bifurcated prosthesis within the corporeal lumen;

(p) removing the delivery assembly from the corporeal lumen; and (q) closing the opening in the corporeal lumen.

8. The method of claim 7, said method further comprising the steps of:

(r) withdrawing the capsule jacket proximally to expose the distal covering device, the bifurcated prosthesis, the contralateral covering device and at least a portion of the ipsilateral covering device after performing step (i) and prior to performing step (j);

(s) removing the superior end of the bifurcated graft from the distal covering device after performing steps (j) and prior to performing step (k);

(t) removing the contralateral end from the contralateral covering device after performing step (l) and prior to performing step (m); and (u) removing the ipsilateral end from the ipsilateral covering device after performing step (n) and prior to performing step (o).

9. A method for emplacement of a bifurcated graft in a corporeal lumen having a wall, the bifurcated graft including an anchoring system and being disposed within a delivery catheter assembly including a balloon catheter having a distal cover, an inflatable member and a first shaft coupled to the distal cover and the inflatable member, the delivery catheter assembly further including a catheter having an ipsilateral cover and second shaft coupled to the ipsilateral cover, the delivery catheter further including a contralateral assembly having a contralateral cover, said method comprising the steps of:

manipulating the delivery catheter assembly to advance the bifurcated graft, the balloon catheter, the ipsilateral cover and the contralateral cover into a corporeal lumen, wherein the bifurcated graft is removably retained in the distal, ipsilateral and contralateral covers to prevent portions of the anchoring system from contacting the corporeal lumen wall while the bifurcated graft is being advanced through the corporeal lumen;

positioning the bifurcated graft at a desired location in the corporeal lumen;

removing the bifurcated graft from the distal, ipsilateral and contralateral covers, inflating the inflatable member to engage the bifurcated graft so that the anchoring system and the bifurcated graft are secured to the corporeal lumen wall;

deflating the inflatable member; and withdrawing the delivery catheter assembly from the bifurcated graft and from the corporeal lumen, wherein the bifurcated graft is retained within the corporeal lumen.

10. The method of claim 9, wherein the delivery catheter assembly further includes a capsule jacket coaxially disposed over the catheter including the ipsilateral cover, and the balloon catheter is coaxially disposed within the catheter including the ipsilateral cover, such that the capsule jacket covers the bifurcated graft, the ipsilateral cover, the contralateral cover and at least a portion of the distal cover, said method further comprising the step of withdrawing the capsule jacket from the bifurcated graft prior to removing the anchoring system from the distal, ipsilateral and contralateral capsules.

11. A method for implanting a bifurcated graft in a corporeal lumen having a wall afflicted by an aneurysm having a superior end, the bifurcated graft including superior, ipsilateral inferior and contralateral inferior ends, an anchoring system having wall engaging members, said method comprising the steps of:

covering the ipsilateral inferior end of the bifurcated graft with an ipsilateral cover, the ipsilateral cover being coupled to a first shaft;

covering the superior end of the bifurcated graft with a distal cover, the distal cover being coupled to a second shaft in fluid communication with a main balloon, wherein the second shaft is coaxially and slidably disposed within the first shaft;

covering the contralateral inferior end of the bifurcated graft with a contralateral cover, the contralateral cover being coupled to a pull wire;

covering the bifurcated graft, the ipsilateral cover, the contralateral cover and at least a portion of the distal cover and pull wire with a sheath slidably disposed over the first and second shafts;

introducing the bifurcated graft, distal cover, ipsilateral cover, contralateral cover, pull wire, balloon and at least a portion of the first shaft, second shaft and sheath into a corporeal lumen;

positioning the bifurcated graft such that the superior end of the graft is located superior to the superior end of the aneurysm;

removing the sheath from the distal cover, the contralateral cover and at least a portion of the ipsilateral cover;

removing the distal cover from the superior end of the graft;

positioning the main balloon adjacent the superior end of the graft; inflating the main balloon to urge the wall engaging members of the an anchoring system into the wall of the lumen;

removing the contralateral cover from the ipsilateral inferior end of the graft and from the corporeal lumen;

inserting an auxiliary balloon into the corporeal lumen adjacent the contralateral inferior end of the graft;

inflating the auxiliary balloon to urge the wall engaging members of the anchoring system into the wall of the lumen;

removing the ipsilateral cover from the ipsilateral inferior end of the graft, deflating the auxiliary balloon;

removing the auxiliary balloon from the corporeal lumen;

deflating the main balloon;

positioning the main balloon adjacent the ipsilateral inferior end of the graft;

inflating the main balloon to urge the wall engaging members of the anchoring system into the wall of the lumen;

deflating the main balloon; and removing the main balloon, distal cover, ipsilateral cover, first shaft, second shaft and sheath from the corporeal lumen, wherein the bifurcated graft is retained in the lumen.

12. The method of claim 11, wherein said introducing the bifurcated graft step includes providing an opening in at least one femoral artery and said positioning the bifurcated graft step includes placing the bifurcated graft proximate an aortic bifurcation.

* * * * *

UNITED STATES PATENT AND TRADEMARK OFFICE
CERTIFICATE OF CORRECTION

PATENT NO.    : 6,322,587 B1                                          Page 1 of 1
DATED         : November 21, 2001
INVENTOR(S)   : Dinah B. Quiachon et al.

It is certified that error appears in the above-identified patent and that said Letters Patent is hereby corrected as shown below:

<u>Title page, Item [54] and Column 1, lines 1-3,</u>
Change title to read: -- METHOD FOR DEPLOYING BIFURCATED GRAFT USING A MULTICAPSULE SYSTEM --.

<u>Column 30,</u>
Line 28, after "balloon;", start a new line with the expression that begins "position the main balloon…".

<u>Column 32,</u>
Line 65, after "graft;", start a new line with the expression that begins "inflating the main balloon…".
Line 66, delete "an" before "anchoring".

Signed and Sealed this

Eighteenth Day of June, 2002

Attest:

Attesting Officer

JAMES E. ROGAN
Director of the United States Patent and Trademark Office